US010098648B2

(12) United States Patent
Meridew

(10) Patent No.: US 10,098,648 B2
(45) Date of Patent: Oct. 16, 2018

(54) PATIENT-SPECIFIC GUIDE FOR PARTIAL ACETABULAR SOCKET REPLACEMENT

(71) Applicant: Biomet Manufacturing, LLC, Warsaw, IN (US)

(72) Inventor: Jason D. Meridew, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 310 days.

(21) Appl. No.: 14/983,077

(22) Filed: Dec. 29, 2015

(65) Prior Publication Data

US 2016/0128706 A1 May 12, 2016

Related U.S. Application Data

(60) Division of application No. 13/088,787, filed on Apr. 18, 2011, now Pat. No. 9,271,744, which is a (Continued)

(51) Int. Cl.
*A61B 17/17* (2006.01)
*A61B 34/10* (2016.01)
(Continued)

(52) U.S. Cl.
CPC .......... *A61B 17/1746* (2013.01); *A61B 34/10* (2016.02); *A61F 2/30756* (2013.01); *A61F 2/34* (2013.01); *A61B 2017/00526* (2013.01); *A61B 2017/568* (2013.01); *A61B 2034/108* (2016.02); *A61F 2/30942* (2013.01);
(Continued)

(58) Field of Classification Search
CPC ........................ A61B 17/1746; A61B 17/1666
See application file for complete search history.

(56) References Cited

U.S. PATENT DOCUMENTS 1,480,285 A 1/1924 Moore
2,181,746 A 11/1939 Siebrandt
(Continued)

FOREIGN PATENT DOCUMENTS

CA 2447694 A1 12/2002
CA 2501041 A1 4/2004
(Continued)

OTHER PUBLICATIONS

"U.S. Appl. No. 12/255,945, Advisory Action dated Feb. 5, 2014", 3 pgs.

(Continued)

*Primary Examiner* — Andrew Yang
(74) *Attorney, Agent, or Firm* — Schwegman Lundberg & Woessner, P.A.

(57) ABSTRACT

A device for partial acetabular replacement includes a patient-specific acetabular guide. The acetabular guide has a first surface configured to nestingly mate in only one position to the patient's acetabulum. The acetabular guide includes a patient-specific guiding formation configured to guide a cutting tool to remove damaged tissue from a defect of the patient's acetabulum and prepare a patient-specific implantation slot corresponding to the defect after removal of the damaged tissue. A patient-specific partial acetabular implant can be configured to nestingly mate with the patient-specific implantation slot.

19 Claims, 5 Drawing Sheets

202
200
204
100
106
104
80
102
82
84
83

Related U.S. Application Data continuation-in-part of application No. 12/893,306, filed on Sep. 29, 2010, now Pat. No. 9,113,971.

(51) Int. Cl.
*A61F 2/30* (2006.01)
*A61F 2/34* (2006.01)
*A61B 17/00* (2006.01)
*A61B 17/56* (2006.01)

(52) U.S. Cl.
CPC ............... *A61F 2002/30878* (2013.01); *A61F 2002/3487* (2013.01); *A61F 2310/00029* (2013.01); *A61F 2310/00161* (2013.01); *A61F 2310/00371* (2013.01)

(56) References Cited

U.S. PATENT DOCUMENTS 2,407,845 A 9/1946 Orisan
2,416,228 A 2/1947 Sheppard
2,618,913 A 11/1952 Plancon et al.
2,910,978 A 11/1959 Urist
3,330,611 A 7/1967 Heifetz
3,840,904 A 10/1974 Tronzo
3,975,858 A 8/1976 Much
4,246,895 A 1/1981 Rehder
4,306,866 A 12/1981 Weissman
4,324,006 A 4/1982 Charnley
4,421,112 A 12/1983 Mains et al.
4,428,571 A 1/1984 Sugarman
4,436,864 A 3/1984 Grossi et al.
4,457,306 A 7/1984 Borzone
4,475,549 A 10/1984 Oh
4,506,393 A 3/1985 Murphy
4,524,766 A 6/1985 Petersen
4,528,980 A 7/1985 Kenna
4,565,191 A 1/1986 Slocum
4,619,658 A 10/1986 Pappas et al.
4,621,630 A 11/1986 Kenna
4,632,111 A 12/1986 Roche
4,633,862 A 1/1987 Petersen
4,663,720 A 5/1987 Duret et al.
4,689,984 A 9/1987 Kellner
4,695,283 A 9/1987 Aldinger
4,696,292 A 9/1987 Heiple
4,703,751 A 11/1987 Pohl
4,704,686 A 11/1987 Aldinger
4,706,660 A 11/1987 Petersen
4,719,907 A 1/1988 Banko et al.
4,721,104 A 1/1988 Kaufman et al.
4,722,330 A 2/1988 Russell et al.
4,759,350 A 7/1988 Dunn et al.
4,778,474 A 10/1988 Homsy
4,800,874 A 1/1989 David et al.
4,821,213 A 4/1989 Cline et al.
4,822,365 A 4/1989 Walker et al.
4,841,975 A 6/1989 Woolson
4,846,161 A 7/1989 Roger
4,871,975 A 10/1989 Nawata et al.
4,892,545 A 1/1990 Day et al.
4,893,619 A 1/1990 Dale et al.
4,896,663 A 1/1990 Vandewalls
4,907,577 A 3/1990 Wu
4,927,422 A 5/1990 Engelhardt
4,936,862 A 6/1990 Walker et al.
4,952,213 A 8/1990 Bowman et al.
4,959,066 A 9/1990 Dunn et al.
4,976,737 A 12/1990 Leake
4,979,949 A 12/1990 Matsen, III et al.
4,985,037 A 1/1991 Petersen
4,994,064 A 2/1991 Aboczky
5,002,579 A 3/1991 Copf et al.
5,006,121 A 4/1991 Hafeli
5,007,936 A 4/1991 Woolson
5,019,105 A 5/1991 Wiley
5,030,219 A 7/1991 Matsen et al.
5,030,221 A 7/1991 Buechel et al.
5,037,424 A 8/1991 Aboczsky
5,041,117 A 8/1991 Engelhardt
5,053,037 A 10/1991 Lackey et al.
5,053,039 A 10/1991 Hofmann et al.
5,056,351 A 10/1991 Stiver et al.
5,061,270 A 10/1991 Aboczky
5,086,401 A 2/1992 Glassman et al.
5,098,383 A 3/1992 Hemmy et al.
5,098,436 A 3/1992 Ferrante et al.
5,108,425 A 4/1992 Hwang
5,122,144 A 6/1992 Bert et al.
5,123,927 A 6/1992 Duncan et al.
5,129,908 A 7/1992 Petersen
5,129,909 A 7/1992 Sutherland
5,133,760 A 7/1992 Petersen et al.
5,140,777 A 8/1992 Ushiyama et al.
5,141,512 A 8/1992 Farmer et al.
5,150,304 A 9/1992 Berchem et al.
5,176,684 A 1/1993 Ferrante et al.
5,176,711 A 1/1993 Grimes
5,194,066 A 3/1993 Van Zile
5,234,433 A 8/1993 Bert
5,246,444 A 9/1993 Schreiber
5,253,506 A 10/1993 Davis
5,258,032 A 11/1993 Bertin
5,261,915 A 11/1993 Durlacher et al.
5,274,565 A 12/1993 Reuben
5,282,802 A 2/1994 Mahony, III
5,299,288 A 3/1994 Glassman
5,300,077 A 4/1994 Howell
5,320,529 A 6/1994 Pompa
5,320,625 A 6/1994 Bertin
5,323,697 A 6/1994 Schrock
5,342,366 A 8/1994 Whiteside et al.
5,344,423 A 9/1994 Dietz et al.
5,360,446 A 11/1994 Kennedy
5,364,402 A 11/1994 Mumme et al.
5,368,858 A 11/1994 Hunziker
5,370,692 A 12/1994 Fink et al.
5,370,699 A 12/1994 Hood
5,405,395 A 4/1995 Coates
5,408,409 A 4/1995 Glassman et al.
5,411,521 A 5/1995 Putnam et al.
5,415,662 A 5/1995 Ferrante et al.
5,417,694 A 5/1995 Marik et al.
5,438,263 A 8/1995 Dworkin et al.
5,440,496 A 8/1995 Andersson et al.
5,448,489 A 9/1995 Reuben
5,449,360 A 9/1995 Schreiber
5,452,407 A 9/1995 Crook
5,454,816 A 10/1995 Ashby
5,462,550 A 10/1995 Dietz et al.
5,472,415 A 12/1995 King et al.
5,474,559 A 12/1995 Bertin et al.
5,490,854 A 2/1996 Fisher et al.
5,496,324 A 3/1996 Barnes
5,507,833 A 4/1996 Bohn
5,514,519 A 5/1996 Neckers
5,520,695 A 5/1996 Luckman
5,527,317 A 6/1996 Ashby et al.
5,539,649 A 7/1996 Walsh et al.
5,540,695 A 7/1996 Levy
5,545,222 A 8/1996 Bonutti
5,549,688 A 8/1996 Ries et al.
5,554,190 A 9/1996 Draenert
5,560,096 A 10/1996 Stephens
5,560,728 A 10/1996 Mcfadden
5,571,110 A 11/1996 Matsen, III et al.
5,571,111 A 11/1996 Aboczky
5,578,037 A 11/1996 Sanders et al.
5,593,411 A 1/1997 Stalcup et al.
5,595,703 A 1/1997 Swaelens et al.
5,601,565 A 2/1997 Huebner
5,607,431 A 3/1997 Dudasik et al.
5,611,802 A 3/1997 Samuelson et al.
5,613,969 A 3/1997 Jenkins, Jr.

(56) References Cited

U.S. PATENT DOCUMENTS 5,616,147 A 4/1997 Gadelius
5,620,448 A 4/1997 Puddu
5,634,927 A 6/1997 Houston et al.
5,641,323 A 6/1997 Caldarise
5,653,714 A 8/1997 Dietz et al.
5,658,294 A 8/1997 Sederholm
5,662,656 A 9/1997 White
5,662,710 A 9/1997 Bonutti
5,671,018 A 9/1997 Ohara et al.
5,676,668 A 10/1997 McCue et al.
5,677,107 A 10/1997 Neckers
5,681,354 A 10/1997 Eckhoff
5,682,886 A 11/1997 Delp et al.
5,683,469 A 11/1997 Johnson et al.
5,690,635 A 11/1997 Matsen, III et al.
5,697,933 A 12/1997 Gundlapalli et al.
5,702,460 A 12/1997 Carls et al.
5,702,464 A 12/1997 Lackey et al.
5,704,941 A 1/1998 Jacober et al.
5,709,689 A 1/1998 Ferrante et al.
5,720,752 A 2/1998 Elliott et al.
5,722,978 A 3/1998 Jenkins, Jr.
5,725,376 A 3/1998 Poirier
5,725,593 A 3/1998 Caracciolo
5,728,128 A 3/1998 Crickenberger et al.
5,735,277 A 4/1998 Schuster
5,745,834 A 4/1998 Bampton et al.
5,748,767 A 5/1998 Raab
5,749,875 A 5/1998 Puddu
5,749,876 A 5/1998 Duvillier et al.
5,762,125 A 6/1998 Mastrorio
5,766,251 A 6/1998 Koshino
5,768,134 A 6/1998 Swaelens et al.
5,769,092 A 6/1998 Williamson, Jr.
5,776,200 A 7/1998 Johnson et al.
5,786,217 A 7/1998 Tubo et al.
5,792,143 A 8/1998 Samuelson et al.
5,798,924 A 8/1998 Eufinger et al.
5,799,055 A 8/1998 Peshkin et al.
5,835,619 A 11/1998 Morimoto et al.
5,860,980 A 1/1999 Axelson, Jr. et al.
5,860,981 A 1/1999 Bertin et al.
5,871,018 A 2/1999 Delp et al.
5,876,456 A 3/1999 Sederholm et al.
5,879,398 A 3/1999 Swarts et al.
5,879,402 A 3/1999 Lawes et al.
5,879,404 A 3/1999 Bateman et al.
5,880,976 A 3/1999 DiGioia III et al.
5,885,297 A 3/1999 Matsen
5,885,298 A 3/1999 Herrington et al.
5,888,219 A 3/1999 Bonutti
5,895,389 A 4/1999 Schenk et al.
5,899,907 A 5/1999 Johnson
5,901,060 A 5/1999 Schall et al.
5,911,724 A 6/1999 Wehrli
5,921,988 A 7/1999 Legrand
5,925,049 A 7/1999 Gustilo et al.
5,925,077 A 7/1999 Williamson et al.
5,942,370 A 8/1999 Neckers
5,967,777 A 10/1999 Klein
5,976,149 A 11/1999 Masini
5,980,526 A 11/1999 Johnson et al.
6,008,433 A 12/1999 Stone
6,013,081 A 1/2000 Burkinshaw et al.
6,019,767 A 2/2000 Howell
6,033,415 A 3/2000 Mittelstadt et al.
6,042,612 A 3/2000 Voydeville
6,056,754 A 5/2000 Haines et al.
6,059,789 A 5/2000 Dinger
6,059,833 A 5/2000 Doets
6,066,175 A 5/2000 Henderson et al.
6,086,593 A 7/2000 Bonutti
6,120,510 A 9/2000 Albrektsson et al.
6,120,544 A 9/2000 Grundei et al.
6,126,690 A 10/2000 Ateshian et al.
6,126,692 A 10/2000 Robie et al.
6,132,469 A 10/2000 Schroeder
6,136,033 A 10/2000 Suemer
6,156,069 A 12/2000 Amstutz
6,159,217 A 12/2000 Robie et al.
6,161,080 A 12/2000 Aouni-Ateshian et al.
6,162,257 A 12/2000 Gustilo et al.
6,187,010 B1 2/2001 Masini
6,195,615 B1 2/2001 Lysen
6,203,546 B1 3/2001 Macmahon
6,205,411 B1 3/2001 Digioia, III et al.
6,206,927 B1 3/2001 Fell et al.
6,210,445 B1 4/2001 Zawadzki
6,238,435 B1 5/2001 Meulink et al.
6,254,604 B1 7/2001 Howell
6,258,097 B1 7/2001 Cook et al.
6,264,698 B1 7/2001 Lawes et al.
6,270,529 B1 8/2001 Terrill-Grisoni et al.
6,273,891 B1 8/2001 Masini
6,290,727 B1 9/2001 Otto et al.
6,293,971 B1 9/2001 Nelson et al.
6,302,913 B1 10/2001 Ripamonti et al.
6,310,269 B1 10/2001 Friese et al.
6,312,258 B1 11/2001 Ashman
6,312,473 B1 11/2001 Oshida
6,319,285 B1 11/2001 Chamier et al.
6,322,728 B1 11/2001 Brodkin et al.
6,325,829 B1 12/2001 Schmotzer
6,327,491 B1 12/2001 Franklin et al.
6,338,738 B1 1/2002 Bellotti et al.
6,343,987 B2 2/2002 Hayama et al.
6,354,011 B1 3/2002 Albrecht
6,361,563 B2 3/2002 Terrill-Grisoni et al.
6,379,299 B1 4/2002 Borodulin et al.
6,379,388 B1 4/2002 Ensign et al.
6,383,228 B1 5/2002 Schmotzer
6,391,251 B1 5/2002 Keicher et al.
6,395,005 B1 5/2002 Lovell
6,416,553 B1 7/2002 White et al.
6,424,332 B1 7/2002 Powell
6,427,698 B1 8/2002 Yoon et al.
6,459,948 B1 10/2002 Ateshian et al.
6,463,351 B1 10/2002 Clynch
6,475,243 B1 11/2002 Sheldon et al.
6,482,236 B2 11/2002 Habecker
6,488,715 B1 12/2002 Pope et al.
6,503,255 B1 1/2003 Albrektsson et al.
6,508,980 B1 1/2003 Sachs et al.
6,510,334 B1 1/2003 Schuster et al.
6,514,259 B2 2/2003 Picard et al.
6,517,583 B1 2/2003 Pope et al.
6,519,998 B2 2/2003 Ertl et al.
6,520,964 B2 2/2003 Tallarida et al.
6,533,737 B1 3/2003 Brosseau et al.
6,547,823 B2 4/2003 Scarborough et al.
6,551,325 B2 4/2003 Neubauer et al.
6,554,837 B1 4/2003 Hauri et al.
6,556,008 B2 4/2003 Thesen
6,558,391 B2 5/2003 Axelson, Jr. et al.
6,558,428 B2 5/2003 Park
6,562,073 B2 5/2003 Foley
6,564,085 B2 5/2003 Meaney et al.
6,567,681 B1 5/2003 Lindequist
6,575,980 B1 6/2003 Robie et al.
6,575,982 B1 6/2003 Bonutti
6,591,581 B2 7/2003 Schmieding
6,605,293 B1 8/2003 Giordano et al.
6,610,067 B2 8/2003 Tallarida et al.
6,622,567 B1 9/2003 Hamel et al.
6,629,999 B1 10/2003 Serafin, Jr.
6,641,617 B1 11/2003 Merrill et al.
6,676,892 B2 1/2004 Das et al.
6,682,566 B2 1/2004 Draenert et al.
6,682,567 B1 1/2004 Schroeder
6,696,073 B2 2/2004 Boyce et al.
6,697,664 B2 2/2004 Kienzle III et al.
6,699,289 B2 3/2004 Iannotti et al.
6,701,174 B1 3/2004 Krause et al.
6,709,462 B2 3/2004 Hanssen

(56) References Cited

U.S. PATENT DOCUMENTS 6,711,431 B2 3/2004 Sarin et al.
6,711,432 B1 3/2004 Krause et al.
6,712,856 B1 3/2004 Carignan et al.
6,716,249 B2 4/2004 Hyde
6,725,077 B1 4/2004 Balloni et al.
6,738,657 B1 5/2004 Franklin et al.
6,740,092 B2 5/2004 Lombardo et al.
6,743,235 B2 6/2004 Subba Rao
6,749,638 B1 6/2004 Saladino
6,750,653 B1 6/2004 Zou et al.
6,772,026 B2 8/2004 Bradbury et al.
6,780,190 B2 8/2004 Maroney
6,786,930 B2 9/2004 Biscup
6,799,066 B2 9/2004 Steines et al.
6,823,871 B2 11/2004 Schmieding
6,827,723 B2 12/2004 Carson
6,887,247 B1 5/2005 Couture et al.
6,905,514 B2 6/2005 Carignan et al.
6,916,324 B2 7/2005 Sanford et al.
6,923,817 B2 8/2005 Carson et al.
6,923,831 B2 8/2005 Fell et al.
6,932,842 B1 8/2005 Litschko et al.
6,942,475 B2 9/2005 Ensign et al.
6,944,518 B2 9/2005 Roose
6,945,976 B2 9/2005 Ball et al.
6,953,480 B2 10/2005 Mears et al.
6,960,216 B2 11/2005 Kolb et al.
6,966,932 B1 11/2005 Schroeder
6,975,755 B1 12/2005 Bamberg
6,990,220 B2 1/2006 Ellis et al.
6,993,406 B1 1/2006 Cesarano, III et al.
7,001,385 B2 2/2006 Bonutti
7,022,141 B2 4/2006 Dwyer et al.
7,029,479 B2 4/2006 Tallarida et al.
7,042,222 B2 5/2006 Zheng et al.
7,048,741 B2 5/2006 Swanson
7,050,877 B2 5/2006 Iseki et al.
7,060,074 B2 6/2006 Rosa et al.
7,074,241 B2 7/2006 Mckinnon
RE39,301 E 9/2006 Bertin
7,104,997 B2 9/2006 Lionberger et al.
7,105,026 B2 9/2006 Johnson et al.
7,115,131 B2 10/2006 Engh et al.
7,121,832 B2 10/2006 Hsieh et al.
7,141,053 B2 11/2006 Rosa et al.
D533,664 S 12/2006 Büttler et al.
7,169,185 B2 1/2007 Sidebotham
7,174,282 B2 2/2007 Hollister et al.
7,176,466 B2 2/2007 Rousso et al.
7,184,814 B2 2/2007 Lang et al.
7,198,628 B2 4/2007 Ondrla et al.
7,218,232 B2 5/2007 Disilvestro et al.
7,220,264 B1 5/2007 Hershberger
7,239,908 B1 7/2007 Alexander et al.
7,241,315 B2 7/2007 Evans
7,255,702 B2 8/2007 Serra et al.
7,258,701 B2 8/2007 Aram et al.
7,275,218 B2 9/2007 Petrella et al.
7,282,054 B2 10/2007 Steffensmeier et al.
7,291,177 B2 11/2007 Gibbs
7,294,133 B2 11/2007 Zink et al.
7,297,164 B2 11/2007 Johnson et al.
7,309,339 B2 12/2007 Cusick et al.
7,333,013 B2 2/2008 Berger
7,335,207 B1 2/2008 Smith
7,335,231 B2 2/2008 Mclean
7,371,260 B2 5/2008 Malinin
7,383,164 B2 6/2008 Aram et al.
7,385,498 B2 6/2008 Dobosz
7,388,972 B2 6/2008 Kitson
7,390,327 B2 6/2008 Collazo et al.
7,392,076 B2 6/2008 Moctezuma De
7,419,492 B2 9/2008 Yoon et al.
7,427,200 B2 9/2008 Noble et al.
7,427,272 B2 9/2008 Richard et al.
7,468,075 B2 12/2008 Lang et al.
7,474,223 B2 1/2009 Nycz et al.
7,488,325 B2 2/2009 Qian et al.
7,494,510 B2 2/2009 Zweymuller
7,517,365 B2 4/2009 Carignan et al.
7,519,540 B2 4/2009 Mayaud
7,527,631 B2 5/2009 Maroney et al.
7,534,263 B2 5/2009 Burdulis, Jr. et al.
7,537,664 B2 5/2009 O'neill et al.
7,542,791 B2 6/2009 Mire et al.
7,559,931 B2 7/2009 Stone
7,575,602 B2 8/2009 Amirouche et al.
7,578,851 B2 8/2009 Dong et al.
7,582,091 B2 9/2009 Duncan et al.
7,591,821 B2 9/2009 Kleman
7,601,155 B2 10/2009 Petersen
7,603,192 B2 10/2009 Martin et al.
7,604,639 B2 10/2009 Swanson
7,611,516 B2 11/2009 Maroney
7,618,451 B2 11/2009 Berez et al.
7,621,915 B2 11/2009 Frederick et al.
7,625,409 B2 12/2009 Saltzman et al.
7,646,161 B2 1/2010 Albu-Schäffer et al.
7,651,501 B2 1/2010 Penenberg et al.
7,670,345 B2 3/2010 Plassky et al.
7,682,398 B2 3/2010 Croxton et al.
7,695,477 B2 4/2010 Creger et al.
7,695,521 B2 4/2010 Ely et al.
7,699,847 B2 4/2010 Sheldon et al.
7,704,253 B2 4/2010 Bastian et al.
7,723,395 B2 5/2010 Ringeisen et al.
7,747,305 B2 6/2010 Dean et al.
D622,854 S 8/2010 Otto et al.
7,780,672 B2 8/2010 Metzger et al.
7,780,740 B2 8/2010 Steinberg
7,789,885 B2 9/2010 Metzger
7,794,466 B2 9/2010 Merchant et al.
7,794,467 B2 9/2010 McGinley et al.
7,794,504 B2 9/2010 Case
7,806,896 B1 10/2010 Bonutti
7,809,184 B2 10/2010 Neubauer et al.
7,819,925 B2 10/2010 King et al.
7,828,806 B2 11/2010 Graf et al.
7,833,245 B2 11/2010 Kaes et al.
7,837,690 B2 11/2010 Metzger
7,850,698 B2 12/2010 Straszheim-Morley et al.
7,854,737 B2 12/2010 Daniels et al.
7,879,109 B2 2/2011 Borden et al.
7,892,261 B2 2/2011 Bonutti
7,896,921 B2 3/2011 Smith et al.
7,926,363 B2 4/2011 Miller et al.
7,935,119 B2 5/2011 Ammann et al.
7,935,150 B2 5/2011 Carignan et al.
7,938,861 B2 5/2011 King et al.
7,959,637 B2 6/2011 Fox et al.
7,962,196 B2 6/2011 Tuma
7,963,968 B2 6/2011 Dees, Jr.
7,967,823 B2 6/2011 Ammann et al.
7,967,868 B2 6/2011 White et al.
7,974,677 B2 7/2011 Mire et al.
7,981,158 B2 7/2011 Fitz et al.
7,988,736 B2 8/2011 May et al.
7,993,353 B2 8/2011 Roβner et al.
8,062,301 B2 11/2011 Ammann et al.
8,066,708 B2 11/2011 Lang et al.
8,070,752 B2 12/2011 Metzger et al.
8,083,745 B2 12/2011 Lang et al.
8,083,746 B2 12/2011 Novak
8,083,749 B2 12/2011 Taber
8,086,336 B2 12/2011 Christensen
8,092,465 B2 1/2012 Metzger et al.
8,105,330 B2 1/2012 Fitz et al.
8,122,582 B2 2/2012 Burdulis, Jr. et al.
8,133,230 B2 3/2012 Stevens et al.
8,133,234 B2 3/2012 Meridew et al.
8,137,406 B2 3/2012 Novak et al.
8,147,861 B2 4/2012 Jones et al.
8,160,345 B2 4/2012 Pavlovskaia et al.
8,167,823 B2 5/2012 Nycz et al.

(56) References Cited

U.S. PATENT DOCUMENTS 8,167,951 B2 5/2012 Ammann
8,170,641 B2 5/2012 Belcher
8,172,850 B2 5/2012 Mcminn
8,182,489 B2 5/2012 Horacek
8,192,441 B2 6/2012 Collazo
8,192,495 B2 6/2012 Simpson et al.
8,200,355 B2 6/2012 Lee et al.
8,211,112 B2 7/2012 Novak et al.
8,221,430 B2 7/2012 Park et al.
8,241,292 B2 8/2012 Collazo
8,241,293 B2 8/2012 Stone et al.
8,246,680 B2 8/2012 Betz et al.
8,260,589 B1 9/2012 Kumar
8,265,790 B2 9/2012 Amiot et al.
8,268,099 B2 9/2012 O'neill et al.
8,268,100 B2 9/2012 O'neill et al.
D669,176 S 10/2012 Frey
8,282,646 B2 10/2012 Schoenefeld et al.
8,298,237 B2 10/2012 Schoenefeld et al.
8,303,596 B2 11/2012 Plaβky et al.
8,313,491 B2 11/2012 Green, II et al.
D672,038 S 12/2012 Frey
8,333,772 B2 12/2012 Fox et al.
8,337,426 B2 12/2012 Nycz
8,337,501 B2 12/2012 Fitz et al.
8,337,503 B2 12/2012 Lian
8,355,773 B2 1/2013 Leitner et al.
8,372,078 B2 2/2013 Collazo
8,377,066 B2 2/2013 Katrana et al.
8,388,690 B2 3/2013 Singhatat et al.
8,398,646 B2 3/2013 Metzger et al.
8,407,067 B2 3/2013 Uthgenannt et al.
8,414,594 B2 4/2013 Berger et al.
8,419,741 B2 4/2013 Carignan et al.
8,425,522 B2 4/2013 Bonutti
8,430,882 B2 4/2013 Lowry et al.
8,430,931 B2 4/2013 Acker et al.
8,439,675 B2 5/2013 De Moyer
8,439,925 B2 5/2013 Marino et al.
8,444,564 B2 5/2013 Mahfouz et al.
8,444,651 B2 5/2013 Kunz et al.
8,457,930 B2 6/2013 Schroeder
8,460,302 B2 6/2013 Park et al.
8,469,961 B2 6/2013 Alleyne et al.
8,473,305 B2 6/2013 Belcher et al.
8,486,150 B2 7/2013 White et al.
8,500,740 B2 8/2013 Bojarski et al.
8,529,578 B2 9/2013 Daniels et al.
8,532,361 B2 9/2013 Pavlovskaia et al.
8,532,806 B1 9/2013 Masson
8,532,807 B2 9/2013 Metzger
8,535,387 B2 9/2013 Meridew et al.
8,543,234 B2 9/2013 Gao
8,545,508 B2 10/2013 Collazo
8,551,099 B2 10/2013 Lang et al.
8,568,487 B2 10/2013 Witt et al.
8,591,516 B2 11/2013 Metzger et al.
8,597,365 B2 12/2013 Meridew
8,603,180 B2 12/2013 White et al.
8,608,748 B2 12/2013 Metzger et al.
8,608,749 B2 12/2013 Meridew et al.
8,617,170 B2 12/2013 Ashby et al.
8,617,174 B2 12/2013 Axelson, Jr. et al.
8,617,175 B2 12/2013 Park et al.
8,632,547 B2 1/2014 Maxson et al.
8,652,142 B2 2/2014 Geissler
8,668,700 B2 3/2014 Catanzarite et al.
8,702,712 B2 4/2014 Jordan et al.
8,702,715 B2 4/2014 Ammann et al.
8,706,285 B2 4/2014 Narainasamy et al.
8,715,289 B2 5/2014 Smith
8,728,387 B2 5/2014 Jones et al.
8,735,773 B2 5/2014 Lang
8,764,760 B2 7/2014 Metzger et al.
8,775,133 B2 7/2014 Schroeder
8,777,875 B2 7/2014 Park
8,828,016 B2 9/2014 Major et al.
8,828,087 B2 9/2014 Stone et al.
8,828,089 B1 9/2014 Perez et al.
8,834,568 B2 9/2014 Shapiro
8,858,561 B2 10/2014 White et al.
8,864,769 B2 10/2014 Stone et al.
8,900,244 B2 12/2014 Meridew et al.
8,903,530 B2 12/2014 Metzger
8,956,364 B2 2/2015 Catanzarite
8,979,936 B2 3/2015 White et al.
9,005,297 B2 4/2015 Katrana et al.
9,060,788 B2 6/2015 Bollinger
9,066,734 B2 6/2015 Schoenefeld et al.
9,113,971 B2 8/2015 Metzger et al.
9,173,661 B2 11/2015 Metzger et al.
9,271,744 B2 3/2016 Meridew
2001/0005797 A1 6/2001 Barlow et al.
2001/0011190 A1 8/2001 Park
2001/0021876 A1 9/2001 Terrill-Grisoni et al.
2001/0054478 A1 12/2001 Watanabe et al.
2002/0007294 A1 1/2002 Bradbury et al.
2002/0029045 A1 3/2002 Bonutti
2002/0052606 A1 5/2002 Bonutti
2002/0059049 A1 5/2002 Bradbury et al.
2002/0082741 A1 6/2002 Mazumder et al.
2002/0087274 A1 7/2002 Alexander et al.
2002/0092532 A1 7/2002 Yoon
2002/0107522 A1 8/2002 Picard et al.
2002/0120342 A1 8/2002 Gibbs
2002/0128872 A1 9/2002 Giammattei
2002/0147415 A1 10/2002 Martelli
2002/0186818 A1 12/2002 Arnaud et al.
2002/0193797 A1 12/2002 Johnson et al.
2002/0198528 A1 12/2002 Engh et al.
2002/0198531 A1 12/2002 Millard et al.
2003/0009171 A1 1/2003 Tornier
2003/0009234 A1 1/2003 Treacy et al.
2003/0011624 A1 1/2003 Ellis
2003/0018338 A1 1/2003 Axelson, Jr. et al.
2003/0039676 A1 2/2003 Boyce et al.
2003/0055502 A1 3/2003 Lang et al.
2003/0074800 A1 4/2003 Huang
2003/0105526 A1 6/2003 Bryant et al.
2003/0109784 A1 6/2003 Loh et al.
2003/0120276 A1 6/2003 Tallarida et al.
2003/0130741 A1 7/2003 McMinn
2003/0139817 A1 7/2003 Tuke et al.
2003/0158606 A1 8/2003 Coon et al.
2003/0171757 A1 9/2003 Coon et al.
2003/0212459 A1 11/2003 Gibbs
2003/0216669 A1 11/2003 Lang et al.
2004/0018144 A1 1/2004 Briscoe
2004/0030245 A1 2/2004 Noble et al.
2004/0054372 A1 3/2004 Corden et al.
2004/0054416 A1 3/2004 Wyss et al.
2004/0068187 A1 4/2004 Krause et al.
2004/0092932 A1 5/2004 Aubin et al.
2004/0098133 A1 5/2004 Carignan et al.
2004/0102852 A1 5/2004 Johnson et al.
2004/0102866 A1 5/2004 Harris et al.
2004/0106926 A1 6/2004 Leitner et al.
2004/0115586 A1 6/2004 Andreiko et al.
2004/0122436 A1 6/2004 Grimm
2004/0122439 A1 6/2004 Dwyer et al.
2004/0128026 A1 7/2004 Harris et al.
2004/0133276 A1 7/2004 Lang et al.
2004/0138754 A1 7/2004 Lang et al.
2004/0143336 A1 7/2004 Burkinshaw
2004/0147927 A1 7/2004 Tsougarakis et al.
2004/0148026 A1 7/2004 Bonutti
2004/0153079 A1 8/2004 Tsougarakis et al.
2004/0153087 A1 8/2004 Sanford et al.
2004/0158254 A1 8/2004 Eisermann
2004/0162619 A1 8/2004 Blaylock et al.
2004/0167390 A1 8/2004 Alexander et al.
2004/0171924 A1 9/2004 Mire et al.
2004/0172137 A1 9/2004 Blaylock et al.
2004/0181144 A1 9/2004 Cinquin et al.

(56) References Cited

U.S. PATENT DOCUMENTS

2004/0193169 A1 9/2004 Schon et al.
2004/0204644 A1 10/2004 Tsougarakis et al.
2004/0204760 A1 10/2004 Fitz et al.
2004/0212586 A1 10/2004 Trueman, III
2004/0220583 A1 11/2004 Pieczynski, II et al.
2004/0225369 A1 11/2004 Lakin et al.
2004/0236341 A1 11/2004 Petersen
2004/0236424 A1 11/2004 Berez et al.
2004/0243481 A1 12/2004 Bradbury et al.
2004/0254584 A1 12/2004 Sarin et al.
2004/0260301 A1 12/2004 Lionberger et al.
2005/0008887 A1 1/2005 Haymann et al.
2005/0010227 A1 1/2005 Paul
2005/0010300 A1 1/2005 Disilvestro et al.
2005/0015022 A1 1/2005 Richard et al.
2005/0019664 A1 1/2005 Matsumoto
2005/0021148 A1 1/2005 Gibbs
2005/0027303 A1 2/2005 Lionberger et al.
2005/0027361 A1 2/2005 Reiley
2005/0043806 A1 2/2005 Cook et al.
2005/0043837 A1 2/2005 Rubbert et al.
2005/0049524 A1 3/2005 Lefevre et al.
2005/0049603 A1 3/2005 Calton et al.
2005/0059873 A1 3/2005 Glozman et al.
2005/0060040 A1 3/2005 Auxepaules et al.
2005/0065628 A1 3/2005 Roose
2005/0070897 A1 3/2005 Petersen
2005/0071015 A1 3/2005 Sekel
2005/0075641 A1 4/2005 Singhatat et al.
2005/0096535 A1 5/2005 De La Barrera
2005/0113841 A1 5/2005 Sheldon et al.
2005/0113846 A1 5/2005 Carson
2005/0119664 A1 6/2005 Carignan et al.
2005/0131662 A1 6/2005 Ascenzi et al.
2005/0137708 A1 6/2005 Clark
2005/0148843 A1* 7/2005 Roose .................... A61B 17/17 600/407
2005/0149042 A1 7/2005 Metzger
2005/0171545 A1 8/2005 Walsh et al.
2005/0177245 A1 8/2005 Leatherbury et al.
2005/0203536 A1 9/2005 Laffargue et al.
2005/0203540 A1 9/2005 Broyles
2005/0209605 A1 9/2005 Grimm et al.
2005/0216305 A1 9/2005 Funderud
2005/0222571 A1 10/2005 Ryan
2005/0222573 A1 10/2005 Branch et al.
2005/0228393 A1 10/2005 Williams, III et al.
2005/0234461 A1 10/2005 Burdulis, Jr.
2005/0234465 A1 10/2005 Mccombs et al.
2005/0234468 A1 10/2005 Carson
2005/0240195 A1 10/2005 Axelson, Jr. et al.
2005/0240267 A1 10/2005 Randall
2005/0244239 A1 11/2005 Shimp
2005/0245934 A1 11/2005 Tuke et al.
2005/0245936 A1 11/2005 Tuke et al.
2005/0251147 A1 11/2005 Novak
2005/0267353 A1 12/2005 Marquart et al.
2005/0267485 A1 12/2005 Cordes et al.
2005/0267584 A1 12/2005 Burdulis, Jr. et al.
2005/0273114 A1 12/2005 Novak
2005/0283252 A1 12/2005 Coon et al.
2005/0283253 A1 12/2005 Coon et al.
2006/0004284 A1 1/2006 Grunschlager et al.
2006/0015120 A1 1/2006 Richard et al.
2006/0030853 A1 2/2006 Haines
2006/0038520 A1 2/2006 Negoro
2006/0052725 A1 3/2006 Santilli
2006/0058803 A1 3/2006 Cuckler et al.
2006/0058809 A1 3/2006 Zink et al.
2006/0058884 A1 3/2006 Aram et al.
2006/0058886 A1 3/2006 Wozencroft
2006/0069444 A1 3/2006 Deffenbaugh
2006/0089621 A1 4/2006 Fard
2006/0093988 A1 5/2006 Swaelens et al.
2006/0094951 A1 5/2006 Dean et al.
2006/0095044 A1 5/2006 Grady et al.
2006/0100832 A1 5/2006 Bowman
2006/0105011 A1 5/2006 Sun et al.
2006/0111722 A1 5/2006 Bouadi
2006/0122616 A1 6/2006 Bennett et al.
2006/0122618 A1 6/2006 Claypool et al.
2006/0136058 A1 6/2006 Pietrzak
2006/0142657 A1 6/2006 Quaid et al.
2006/0147332 A1 7/2006 Jones et al.
2006/0149283 A1 7/2006 May et al.
2006/0155380 A1 7/2006 Clemow et al.
2006/0161165 A1 7/2006 Swanson et al.
2006/0161167 A1 7/2006 Myers et al.
2006/0172263 A1 8/2006 Quadling et al.
2006/0178497 A1 8/2006 Gevaert et al.
2006/0184177 A1 8/2006 Echeverri
2006/0184250 A1 8/2006 Bandoh et al.
2006/0190086 A1 8/2006 Clemow et al.
2006/0192319 A1 8/2006 Solar
2006/0195111 A1 8/2006 Couture
2006/0195194 A1 8/2006 Gunther
2006/0195198 A1 8/2006 James
2006/0198943 A1 9/2006 Kumar
2006/0200158 A1 9/2006 Farling et al.
2006/0204932 A1 9/2006 Haymann et al.
2006/0210644 A1 9/2006 Levin
2006/0217808 A1 9/2006 Novak et al.
2006/0235421 A1 10/2006 Rosa et al.
2006/0241635 A1 10/2006 Stumpo et al.
2006/0241636 A1 10/2006 Novak et al.
2006/0271058 A1 11/2006 Ashton et al.
2006/0276796 A1 12/2006 Creger et al.
2006/0276797 A1 12/2006 Botimer
2006/0287733 A1 12/2006 Bonutti
2006/0287891 A1 12/2006 Grasso et al.
2006/0293681 A1 12/2006 Claypool et al.
2007/0015995 A1 1/2007 Lang et al.
2007/0016008 A1 1/2007 Schoenefeld
2007/0016209 A1 1/2007 Ammann et al.
2007/0027680 A1 2/2007 Ashley et al.
2007/0039205 A1 2/2007 Erb et al.
2007/0043582 A1 2/2007 Peveto et al.
2007/0066917 A1 3/2007 Hodorek et al.
2007/0073133 A1 3/2007 Schoenefeld
2007/0073136 A1 3/2007 Metzger
2007/0073137 A1 3/2007 Schoenefeld
2007/0083214 A1 4/2007 Duncan et al.
2007/0083266 A1 4/2007 Lang
2007/0100258 A1 5/2007 Shoham et al.
2007/0100450 A1 5/2007 Hodorek
2007/0100462 A1 5/2007 Lang et al.
2007/0106299 A1 5/2007 Manspeizer
2007/0106391 A1 5/2007 Ronk
2007/0118055 A1 5/2007 Mccombs
2007/0118138 A1 5/2007 Seo et al.
2007/0118243 A1 5/2007 Schroeder et al.
2007/0129809 A1 6/2007 Meridew et al.
2007/0142914 A1 6/2007 Jones et al.
2007/0150068 A1 6/2007 Dong et al.
2007/0156066 A1 7/2007 Mcginley et al.
2007/0156171 A1 7/2007 Lang et al.
2007/0162038 A1 7/2007 Tuke
2007/0162039 A1 7/2007 Wozencroft
2007/0173946 A1 7/2007 Bonutti
2007/0173948 A1 7/2007 Meridew et al.
2007/0185498 A2 8/2007 Lavallee
2007/0191962 A1 8/2007 Jones et al.
2007/0198022 A1 8/2007 Lang et al.
2007/0203430 A1 8/2007 Lang et al.
2007/0203583 A1 8/2007 Slone
2007/0203605 A1 8/2007 Melton et al.
2007/0219562 A1 9/2007 Slone et al.
2007/0219639 A1 9/2007 Otto et al.
2007/0219640 A1 9/2007 Steinberg
2007/0224238 A1 9/2007 Mansmann et al.
2007/0226986 A1 10/2007 Park et al.
2007/0233121 A1 10/2007 Carson et al.
2007/0233136 A1 10/2007 Wozencroft
2007/0233140 A1 10/2007 Metzger et al.

(56) References Cited

U.S. PATENT DOCUMENTS

2007/0233141 A1 10/2007 Park et al.
2007/0233269 A1 10/2007 Steines et al.
2007/0233272 A1 10/2007 Boyce et al.
2007/0238069 A1 10/2007 Lovald et al.
2007/0239282 A1 10/2007 Caylor et al.
2007/0239481 A1 10/2007 Disilvestro et al.
2007/0244487 A1 10/2007 Ammann et al.
2007/0250169 A1 10/2007 Lang
2007/0250175 A1 10/2007 Meridew et al.
2007/0253617 A1 11/2007 Arata et al.
2007/0255288 A1 11/2007 Mahfouz et al.
2007/0255412 A1 11/2007 Hajaj et al.
2007/0262867 A1 11/2007 Westrick et al.
2007/0272747 A1 11/2007 Woods et al.
2007/0276224 A1 11/2007 Lang et al.
2007/0276400 A1 11/2007 Moore et al.
2007/0276501 A1 11/2007 Betz et al.
2007/0288029 A1 12/2007 Justin et al.
2007/0288030 A1 12/2007 Metzger et al.
2008/0009874 A1 1/2008 Meridew et al.
2008/0009952 A1 1/2008 Hodge
2008/0015599 A1 1/2008 D'alessio et al.
2008/0015603 A1 1/2008 Collazo
2008/0015604 A1 1/2008 Collazo
2008/0015605 A1 1/2008 Collazo
2008/0021299 A1 1/2008 Meulink
2008/0021494 A1 1/2008 Schmelzeisen-redeker et al.
2008/0021567 A1 1/2008 Meulink et al.
2008/0027563 A1 1/2008 Johnson et al.
2008/0033442 A1 2/2008 Amiot et al.
2008/0039850 A1 2/2008 Rowley et al.
2008/0051799 A1 2/2008 Bonutti et al.
2008/0051910 A1 2/2008 Kammerzell et al.
2008/0058945 A1 3/2008 Hajaj et al.
2008/0058947 A1 3/2008 Earl et al.
2008/0062183 A1 3/2008 Swaelens
2008/0065225 A1 3/2008 Wasielewski et al.
2008/0094396 A1 4/2008 Sabczynsdi et al.
2008/0097451 A1 4/2008 Chen et al.
2008/0112996 A1 5/2008 Harlow et al.
2008/0114370 A1 5/2008 Schoenefeld
2008/0133022 A1 6/2008 Caylor
2008/0140081 A1 6/2008 Heavener et al.
2008/0140209 A1 6/2008 Iannotti et al.
2008/0140213 A1 6/2008 Ammann et al.
2008/0146969 A1 6/2008 Kurtz
2008/0147072 A1 6/2008 Park et al.
2008/0147073 A1 6/2008 Ammann et al.
2008/0147074 A1 6/2008 Ammann et al.
2008/0161815 A1 7/2008 Schoenefeld et al.
2008/0161816 A1 7/2008 Stevens et al.
2008/0172125 A1 7/2008 Ek
2008/0195099 A1 8/2008 Minas
2008/0195107 A1 8/2008 Cuckler et al.
2008/0195108 A1 8/2008 Bhatnagar et al.
2008/0195109 A1 8/2008 Hunter et al.
2008/0195216 A1 8/2008 Philipp
2008/0200926 A1 8/2008 Verard et al.
2008/0208200 A1 8/2008 Crofford
2008/0208353 A1 8/2008 Kumar et al.
2008/0215059 A1 9/2008 Carignan et al.
2008/0221699 A1 9/2008 Meridew et al.
2008/0230422 A1 9/2008 Pleil et al.
2008/0234664 A1 9/2008 May et al.
2008/0234683 A1 9/2008 May
2008/0234685 A1 9/2008 Gjerde
2008/0234833 A1 9/2008 Bandoh et al.
2008/0243127 A1 10/2008 Lang et al.
2008/0255674 A1 10/2008 Rahaman et al.
2008/0257363 A1 10/2008 Schoenefeld et al.
2008/0262499 A1 10/2008 Giori et al.
2008/0262500 A1 10/2008 Collazo
2008/0262624 A1 10/2008 White et al.
2008/0269596 A1 10/2008 Revie et al.
2008/0269906 A1 10/2008 Iannotti et al.
2008/0275452 A1 11/2008 Lang et al.
2008/0281328 A1 11/2008 Lang et al.
2008/0281329 A1 11/2008 Fitz et al.
2008/0281426 A1 11/2008 Fitz et al.
2008/0287926 A1 11/2008 Abou El Kheir
2008/0287954 A1 11/2008 Kunz et al.
2008/0294170 A1 11/2008 O'brien
2008/0294266 A1 11/2008 Steinberg
2008/0300600 A1 12/2008 Guelat et al.
2008/0306485 A1 12/2008 Coon et al.
2008/0306558 A1 12/2008 Hakki
2008/0312659 A1 12/2008 Metzger et al.
2008/0319448 A1 12/2008 Lavallee et al.
2009/0012526 A1 1/2009 Fletcher
2009/0018546 A1 1/2009 Daley
2009/0018666 A1 1/2009 Grundei et al.
2009/0024131 A1 1/2009 Metzger et al.
2009/0024169 A1 1/2009 Triplett et al.
2009/0043556 A1 2/2009 Axelson et al.
2009/0048618 A1 2/2009 Harrison et al.
2009/0076371 A1 3/2009 Lang et al.
2009/0076512 A1 3/2009 Ammann et al.
2009/0076520 A1 3/2009 Choi
2009/0076555 A1 3/2009 Lowry et al.
2009/0082770 A1 3/2009 Worner et al.
2009/0082774 A1 3/2009 Oti et al.
2009/0087276 A1 4/2009 Rose
2009/0088674 A1 4/2009 Caillouette et al.
2009/0088753 A1 4/2009 Aram et al.
2009/0088754 A1 4/2009 Aker et al.
2009/0088755 A1 4/2009 Aker et al.
2009/0088758 A1 4/2009 Bennett
2009/0088759 A1 4/2009 Aram et al.
2009/0088760 A1 4/2009 Aram et al.
2009/0088761 A1 4/2009 Roose et al.
2009/0088763 A1 4/2009 Aram et al.
2009/0088865 A1 4/2009 Brehm
2009/0088866 A1 4/2009 Case
2009/0089034 A1 4/2009 Penney et al.
2009/0089081 A1 4/2009 Haddad
2009/0093815 A1 4/2009 Fletcher et al.
2009/0093816 A1 4/2009 Roose et al.
2009/0096613 A1 4/2009 Westrick
2009/0099567 A1 4/2009 Zajac
2009/0105837 A1 4/2009 Lafosse et al.
2009/0116621 A1 5/2009 Yuan et al.
2009/0118736 A1 5/2009 Kreuzer
2009/0118769 A1 5/2009 Sixto, Jr. et al.
2009/0129067 A1 5/2009 Fan et al.
2009/0131941 A1 5/2009 Park et al.
2009/0131942 A1 5/2009 Aker et al.
2009/0138020 A1 5/2009 Park et al.
2009/0149964 A1 6/2009 May et al.
2009/0149965 A1 6/2009 Quaid
2009/0149977 A1 6/2009 Schendel
2009/0151736 A1 6/2009 Belcher et al.
2009/0157083 A1 6/2009 Park et al.
2009/0163922 A1 6/2009 Meridew et al.
2009/0163923 A1 6/2009 Flett et al.
2009/0164024 A1 6/2009 Rudan et al.
2009/0177282 A1 7/2009 Bureau et al.
2009/0187193 A1 7/2009 Maroney et al.
2009/0204225 A1 8/2009 Meridew et al.
2009/0209884 A1 8/2009 Van Vorhis et al.
2009/0209961 A1 8/2009 Ferrante et al.
2009/0210067 A1 8/2009 Meridew
2009/0222014 A1 9/2009 Bojarski et al.
2009/0222015 A1 9/2009 Park et al.
2009/0222016 A1 9/2009 Park et al.
2009/0222103 A1 9/2009 Fitz et al.
2009/0226068 A1 9/2009 Fitz et al.
2009/0228016 A1 9/2009 Alvarez
2009/0234360 A1 9/2009 Alexander
2009/0248044 A1 10/2009 Amiot et al.
2009/0250413 A1 10/2009 Hoeppner
2009/0254093 A1 10/2009 White et al.
2009/0254367 A1 10/2009 Belcher et al.
2009/0259312 A1 10/2009 Shterling et al.
2009/0270868 A1 10/2009 Park et al.

(56) References Cited

U.S. PATENT DOCUMENTS

2009/0274350 A1 11/2009 Pavlovskaia et al.
2009/0287217 A1 11/2009 Ammann et al.
2009/0287309 A1 11/2009 Walch et al.
2009/0306676 A1 12/2009 Lang et al.
2009/0307893 A1 12/2009 Burdulis, Jr. et al.
2009/0318836 A1 12/2009 Stone et al.
2009/0318921 A1 12/2009 White et al.
2010/0010493 A1 1/2010 Dower
2010/0015082 A1 1/2010 Ting-Jenulis et al.
2010/0016984 A1 1/2010 Trabish
2010/0016986 A1 1/2010 Trabish
2010/0023015 A1 1/2010 Park
2010/0030231 A1 2/2010 Revie et al.
2010/0036404 A1 2/2010 Yi et al.
2010/0042105 A1 2/2010 Park et al.
2010/0049195 A1 2/2010 Park et al.
2010/0049327 A1 2/2010 Isch et al.
2010/0057088 A1 3/2010 Shah
2010/0076439 A1 3/2010 Hatch
2010/0076505 A1 3/2010 Borja
2010/0076563 A1 3/2010 Otto et al.
2010/0076571 A1 3/2010 Hatch
2010/0082034 A1 4/2010 Remia
2010/0082035 A1 4/2010 Keefer
2010/0082067 A1 4/2010 Kondrashov
2010/0087829 A1 4/2010 Metzger et al.
2010/0094295 A1 4/2010 Schnieders et al.
2010/0099977 A1 4/2010 Hershberger
2010/0105011 A1 4/2010 Karkar et al.
2010/0121334 A1 5/2010 Couture et al.
2010/0121335 A1 5/2010 Penenberg et al.
2010/0131073 A1 5/2010 Meridew et al.
2010/0136214 A1 6/2010 Kumar
2010/0137869 A1 6/2010 Borja et al.
2010/0137924 A1 6/2010 Tuke et al.
2010/0145343 A1 6/2010 Johnson et al.
2010/0145344 A1 6/2010 Jordan et al.
2010/0145466 A1 6/2010 Slone
2010/0152782 A1 6/2010 Stone et al.
2010/0160917 A1 6/2010 Fitz et al.
2010/0160919 A1 6/2010 Axelson, Jr. et al.
2010/0168752 A1 7/2010 Edwards
2010/0168754 A1 7/2010 Fitz et al.
2010/0168857 A1 7/2010 Hatch
2010/0168866 A1 7/2010 Shih
2010/0179663 A1 7/2010 Steinberg
2010/0185202 A1 7/2010 Lester et al.
2010/0191244 A1 7/2010 White et al.
2010/0198067 A1 8/2010 Mahfouz et al.
2010/0198224 A1 8/2010 Metzger
2010/0212138 A1 8/2010 Carroll et al.
2010/0217109 A1 8/2010 Belcher
2010/0217270 A1 8/2010 Polinski et al.
2010/0217336 A1 8/2010 Crawford et al.
2010/0217338 A1 8/2010 Carroll et al.
2010/0217399 A1 8/2010 Groh
2010/0228257 A1 9/2010 Bonutti
2010/0249657 A1 9/2010 Nycz et al.
2010/0249796 A1 9/2010 Nycz
2010/0256649 A1 10/2010 Capsal et al.
2010/0262150 A1 10/2010 Lian
2010/0274253 A1 10/2010 Ure
2010/0281678 A1 11/2010 Burdulis, Jr. et al.
2010/0286700 A1 11/2010 Snider et al.
2010/0286789 A1 11/2010 Meridew
2010/0291401 A1 11/2010 Medina et al.
2010/0292743 A1 11/2010 Singhal et al.
2010/0298894 A1 11/2010 Bojarski et al.
2010/0305574 A1 12/2010 Fitz et al.
2010/0318088 A1 12/2010 Warne et al.
2010/0324692 A1 12/2010 Uthgenannt et al.
2011/0004317 A1 1/2011 Hacking et al.
2011/0008754 A1 1/2011 Bassett et al.
2011/0009869 A1 1/2011 Marino et al.
2011/0014081 A1 1/2011 Jones et al.
2011/0015636 A1 1/2011 Katrana et al.
2011/0015637 A1 1/2011 De Smedt et al.
2011/0015639 A1 1/2011 Metzger et al.
2011/0015752 A1 1/2011 Meridew
2011/0015753 A1 1/2011 Meridew
2011/0016690 A1 1/2011 Narainasamy et al.
2011/0022049 A1 1/2011 Huebner et al.
2011/0022174 A1 1/2011 Holdstein et al.
2011/0029088 A1 2/2011 Rauscher et al.
2011/0029091 A1 2/2011 Bojarski et al.
2011/0029093 A1 2/2011 Bojarski
2011/0029116 A1 2/2011 Jordan et al.
2011/0035012 A1 2/2011 Linares
2011/0040303 A1 2/2011 Iannotti
2011/0040334 A1 2/2011 Kaes et al.
2011/0046735 A1 2/2011 Metzger et al.
2011/0054478 A1 3/2011 Vanasse et al.
2011/0066193 A1 3/2011 Lang et al.
2011/0066245 A1 3/2011 Lang et al.
2011/0071528 A1 3/2011 Carson
2011/0071529 A1 3/2011 Carson
2011/0071530 A1 3/2011 Carson
2011/0071532 A1 3/2011 Carson
2011/0071533 A1 3/2011 Metzger et al.
2011/0071581 A1 3/2011 Lang et al.
2011/0071802 A1 3/2011 Bojarski et al.
2011/0087332 A1 4/2011 Bojarski et al.
2011/0092804 A1 4/2011 Schoenefeld et al.
2011/0093086 A1 4/2011 Witt et al.
2011/0106093 A1 5/2011 Romano et al.
2011/0106254 A1 5/2011 Abel et al.
2011/0125264 A1 5/2011 Bagga et al.
2011/0125284 A1 5/2011 Gabbrielli et al.
2011/0130795 A1 6/2011 Ball
2011/0151027 A1 6/2011 Clineff et al.
2011/0151259 A1 6/2011 Jarman-smith et al.
2011/0153025 A1 6/2011 Mcminn
2011/0160736 A1 6/2011 Meridew et al.
2011/0160867 A1 6/2011 Meridew et al.
2011/0166578 A1 7/2011 Stone et al.
2011/0172672 A1 7/2011 Dubeau et al.
2011/0177590 A1 7/2011 Clyne et al.
2011/0184419 A1 7/2011 Meridew et al.
2011/0184424 A1 7/2011 Isch et al.
2011/0184526 A1 7/2011 White et al.
2011/0190899 A1 8/2011 Pierce et al.
2011/0190901 A1 8/2011 Weissberg et al.
2011/0213376 A1 9/2011 Maxson et al.
2011/0214279 A1 9/2011 Park et al.
2011/0218545 A1 9/2011 Catanzarite et al.
2011/0224674 A1 9/2011 White et al.
2011/0238071 A1 9/2011 Fernandez-Scoma
2011/0245835 A1 10/2011 Dodds et al.
2011/0251617 A1 10/2011 Ammann et al.
2011/0257657 A1 10/2011 Turner et al.
2011/0269100 A1 11/2011 Furrer et al.
2011/0275032 A1 11/2011 Tardieu et al.
2011/0276053 A1 11/2011 Birkbeck et al.
2011/0276145 A1 11/2011 Carignan et al.
2011/0282473 A1 11/2011 Pavlovskaia et al.
2011/0295887 A1 12/2011 Palmese et al.
2011/0313424 A1 12/2011 Bono et al.
2011/0319745 A1 12/2011 Frey
2012/0010619 A1 1/2012 Barsoum
2012/0010710 A1 1/2012 Frigg
2012/0010711 A1 1/2012 Antonyshyn et al.
2012/0029345 A1 2/2012 Mahfouz et al.
2012/0029520 A1 2/2012 Lang et al.
2012/0041445 A1 2/2012 Roose et al.
2012/0041446 A1 2/2012 Wong et al.
2012/0041564 A1 2/2012 Landon
2012/0065640 A1 3/2012 Metzger et al.
2012/0078254 A1 3/2012 Ashby et al.
2012/0078258 A1 3/2012 Lo et al.
2012/0078259 A1 3/2012 Meridew
2012/0089595 A1 4/2012 Jaecksch et al.
2012/0101586 A1 4/2012 Carson
2012/0109137 A1 5/2012 Iannotti et al.
2012/0109138 A1 5/2012 Meridew et al.

(56) References Cited

U.S. PATENT DOCUMENTS

2012/0109226 A1 5/2012 Iannotti et al.
2012/0116203 A1 5/2012 Vancraen et al.
2012/0123422 A1 5/2012 Agnihotri et al.
2012/0123423 A1 5/2012 Fryman
2012/0130382 A1 5/2012 Iannotti et al.
2012/0136365 A1 5/2012 Iannotti et al.
2012/0141034 A1 6/2012 Iannotti et al.
2012/0143197 A1 6/2012 Lang et al.
2012/0143267 A1 6/2012 Iannotti et al.
2012/0150242 A1 6/2012 Mannion
2012/0158002 A1 6/2012 Carignan et al.
2012/0165954 A1 6/2012 Nimal
2012/0190971 A1 7/2012 De
2012/0192401 A1 8/2012 Pavlovskaia et al.
2012/0209276 A1 8/2012 Schuster
2012/0215225 A1 8/2012 Philippon et al.
2012/0215310 A1 8/2012 Sharp et al.
2012/0221017 A1 8/2012 Bonutti
2012/0226283 A1 9/2012 Meridew et al.
2012/0232596 A1 9/2012 Ribeiro
2012/0245587 A1 9/2012 Fang et al.
2012/0245647 A1 9/2012 Kunz et al.
2012/0259335 A1 10/2012 Scifert et al.
2012/0265208 A1 10/2012 Smith
2012/0271131 A1 10/2012 Kling et al.
2012/0271314 A1 10/2012 Stemniski et al.
2012/0271366 A1 10/2012 Katrana et al.
2012/0276509 A1 11/2012 Iannotti et al.
2012/0277751 A1 11/2012 Catanzarite et al.
2012/0289965 A1 11/2012 Gelaude et al.
2012/0296339 A1 11/2012 Iannotti et al.
2012/0303004 A1 11/2012 Uthgenannt et al.
2012/0303033 A1 11/2012 Uthgenannt et al.
2012/0310364 A1 12/2012 Li et al.
2012/0310399 A1 12/2012 Metzger
2012/0316564 A1 12/2012 Serbousek et al.
2012/0323246 A1 12/2012 Catanzarite et al.
2012/0323282 A1 12/2012 Brianza et al.
2012/0323323 A1 12/2012 Vargas et al.
2012/0330319 A1 12/2012 Birkbeck et al.
2013/0001121 A1 1/2013 Metzger
2013/0006250 A1 1/2013 Metzger et al.
2013/0018483 A1 1/2013 Li et al.
2013/0035766 A1 2/2013 Meridew
2013/0046310 A1 2/2013 Ranawat et al.
2013/0053854 A1 2/2013 Schoenefeld et al.
2013/0056912 A1 3/2013 O'neill et al.
2013/0060253 A1 3/2013 Couture et al.
2013/0066323 A1 3/2013 Nycz et al.
2013/0072940 A1 3/2013 Dawood et al.
2013/0085500 A1 4/2013 Meridew et al.
2013/0085590 A1 4/2013 Bryan et al.
2013/0110116 A1 5/2013 Kehres et al.
2013/0110470 A1 5/2013 Vanasse et al.
2013/0116699 A1 5/2013 Smith et al.
2013/0119579 A1 5/2013 Iannotti et al.
2013/0123850 A1 5/2013 Schoenefeld et al.
2013/0131681 A1 5/2013 Katrana et al.
2013/0144392 A1 6/2013 Hughes
2013/0158671 A1 6/2013 Uthgenannt et al.
2013/0197528 A1 8/2013 Zakaria et al.
2013/0197529 A1 8/2013 Metzger
2013/0197687 A1 8/2013 Pavlovskaia et al.
2013/0218163 A1 8/2013 Frey
2013/0245631 A1 9/2013 Bettenga
2013/0245801 A1 9/2013 Schroeder
2013/0261503 A1 10/2013 Sherman
2013/0264749 A1 10/2013 Jones et al.
2013/0268085 A1 10/2013 Dong
2013/0289730 A1 10/2013 Gabriel et al.
2013/0292870 A1 11/2013 Roger
2013/0317511 A1 11/2013 Bojarski et al.
2013/0317621 A1 11/2013 Metzger et al.
2013/0326878 A1 12/2013 Boehm et al.
2013/0338673 A1 12/2013 Keppler
2014/0005672 A1 1/2014 Edwards et al.
2014/0012266 A1 1/2014 Bonin, Jr. et al.
2014/0018934 A1 1/2014 Meridew et al.
2014/0052270 A1 2/2014 Witt et al.
2014/0066937 A1 3/2014 Wiebe, III et al.
2014/0081275 A1 3/2014 Metzger et al.
2014/0081659 A1 3/2014 Nawana et al.
2014/0088724 A1 3/2014 Meridew
2014/0094816 A1 4/2014 White et al.
2014/0100578 A1 4/2014 Metzger et al.
2014/0107651 A1 4/2014 Meridew et al.
2014/0107654 A1 4/2014 Kehres et al.
2014/0107715 A1 4/2014 Heilman et al.
2014/0127211 A1 5/2014 Geles et al.
2014/0135775 A1 5/2014 Maxson et al.
2014/0163564 A1 6/2014 Bollinger
2014/0163565 A1 6/2014 Bollinger
2014/0172116 A1 6/2014 Maxson et al.
2014/0188119 A1 7/2014 Catanzarite et al.
2014/0222157 A1 8/2014 Al Hares et al.
2014/0243833 A1 8/2014 Smith
2014/0257304 A1 9/2014 Eash
2014/0257508 A1 9/2014 Bojarski et al.
2014/0276854 A1 9/2014 Schoenefeld et al.
2014/0276856 A1 9/2014 Schoenefeld
2014/0276870 A1 9/2014 Eash
2014/0276873 A1 9/2014 Meridew et al.
2014/0303938 A1 10/2014 Schoenefeld et al.
2014/0303990 A1 10/2014 Schoenefeld et al.
2014/0309644 A1 10/2014 Metzger et al.
2014/0324058 A1 10/2014 Metzger et al.
2014/0378979 A1 12/2014 Stone et al.
2015/0088293 A1 3/2015 Metzger
2015/0112348 A1 4/2015 Schoenefeld et al.
2015/0150688 A1 6/2015 Vanasse et al.
2015/0157341 A1 6/2015 Catanzarite et al.
2015/0320429 A1 11/2015 Katrana et al.
2015/0320508 A1 11/2015 White et al.
2015/0335438 A1 11/2015 Pierce et al.
2015/0351778 A1 12/2015 Uthgenannt et al.
2016/0038160 A1 2/2016 Metzger et al.

FOREIGN PATENT DOCUMENTS

CA 2505371 A1 5/2004
CA 2505419 A1 6/2004
CA 2506849 A1 6/2004
CA 2546958 A1 6/2005
CA 2546965 A1 6/2005
CA 2588907 A1 6/2006
CA 2590534 A1 6/2006
CN 1630495 A 6/2005
CN 1728976 A 2/2006
CN 1729483 A 2/2006
CN 1729484 A 2/2006
CN 1913844 A 2/2007
CN 101111197 A 1/2008
CN 102038553 A 5/2011
CN 102335742 A 2/2012
DE 3447365 A1 7/1986
DE 04219939 A1 12/1993
DE 4421153 A1 12/1995
DE 10341187 A1 3/2005
DE 102009028503 A1 2/2011
DE 102011082902 A1 3/2012
DE 102012205820 A1 10/2012
DE 112010003901 T5 11/2012
EP 0114505 A1 8/1984
EP 0255797 A1 2/1988
EP 0326768 A2 8/1989
EP 0579868 A2 1/1994
EP 0591985 A1 4/1994
EP 0645984 A1 4/1995
EP 0650706 A1 5/1995
EP 0916324 A2 5/1999
EP 1321107 A1 6/2003
EP 1327424 A1 7/2003
EP 1437102 A1 7/2004
EP 01486900 A1 12/2004

(56) References Cited

FOREIGN PATENT DOCUMENTS

EP 1634551 A2 3/2006
EP 1832239 A1 9/2007
EP 1852072 A2 11/2007
EP 2029061 A1 3/2009
EP 2168507 A2 3/2010
EP 2303146 A1 4/2011
EP 2303192 A1 4/2011
EP 2352445 A1 8/2011
EP 2396741 A1 12/2011
EP 2398381 A1 12/2011
EP 2403437 A2 1/2012
EP 2491873 A2 8/2012
EP 2502582 A1 9/2012
EP 2709568 A1 3/2014
EP 2816962 A1 12/2014
FR 2659226 A2 9/1991
FR 2721195 A1 12/1995
FR 2768916 A1 4/1999
FR 2979817 A1 3/2013
GB 2094590 A 9/1982
GB 2197790 A1 6/1988
GB 2442441 A 4/2008
GB 2447702 A 9/2008
GB 2483980 A 3/2012
GB 2486390 A 6/2012
GB 2490220 A 10/2012
GB 2491526 A 12/2012
JP 59157715 A 9/1984
JP 60231208 A 11/1985
JP 6233790 A 8/1994
JP 2000245758 A 9/2000
JP 2005218861 A 8/2005
JP 2009514612 A 4/2009
JP 2009515610 A 4/2009
JP 2011505080 A 2/2011
JP 2011527885 A 11/2011
JP 5710014 B2 4/2015
KR 20050072500 A 7/2005
KR 20050084024 A 8/2005
RU 2083179 C1 7/1997
RU 2113182 C1 6/1998
RU 2125835 C1 2/1999
RU 2138223 C1 9/1999
RU 2175534 C2 11/2001
RU 2187975 C1 8/2002
RU 2218242 C2 12/2003
TW 231755 A 5/2005
TW 201114409 A 5/2011
WO WO-8807840 A1 10/1988
WO WO-9107139 A1 5/1991
WO WO-9325157 A1 12/1993
WO WO-9528688 A1 10/1995
WO WO-9952473 A1 10/1999
WO WO-9959106 A1 11/1999
WO WO-0170142 A1 9/2001
WO WO-0184479 A1 11/2001
WO WO-0217821 A2 3/2002
WO WO-2002026145 A1 4/2002
WO WO-0236024 A1 5/2002
WO WO-02096268 A2 12/2002
WO WO-03051210 A2 6/2003
WO WO-03051211 A1 6/2003
WO WO 2004032806 A1 4/2004
WO WO 2004049981 A2 6/2004
WO WO-2004051301 A1 6/2004
WO WO-2004078069 A2 9/2004
WO WO-2005051233 A2 6/2005
WO WO-2005051239 A1 6/2005
WO WO-2005051240 A1 6/2005
WO WO-2005077039 A2 8/2005
WO WO-06058057 A2 6/2006
WO WO-06060795 A1 6/2006
WO WO-2006058057 A2 6/2006
WO WO-2006092600 A1 9/2006
WO WO-2006127486 A2 11/2006
WO WO-2006134345 A1 12/2006
WO WO-2006136955 A1 12/2006
WO WO-07041375 A2 4/2007
WO WO-2007053572 A2 5/2007
WO WO-2007062079 A2 5/2007
WO WO 2007092841 A1 8/2007
WO WO-2007137327 A1 12/2007
WO WO-2007145937 A2 12/2007
WO WO-2008014618 A1 2/2008
WO WO-2008021494 A2 2/2008
WO WO-2008040961 A1 4/2008
WO WO-2008044055 A1 4/2008
WO WO-2008091358 A1 7/2008
WO WO-2008101090 A2 8/2008
WO WO-2008109751 A1 9/2008
WO WO-2008112996 A1 9/2008
WO WO-2008140748 A1 11/2008
WO WO-2009001083 A1 12/2008
WO WO-2009001109 A1 12/2008
WO WO-2009025783 A1 2/2009
WO WO-2009073781 A2 6/2009
WO WO-2009129063 A1 10/2009
WO WO-2009129067 A1 10/2009
WO WO-2010033431 A1 3/2010
WO WO-2010088696 A1 8/2010
WO WO-2010093902 A1 8/2010
WO WO-2010096553 A1 8/2010
WO WO-2010096557 A2 8/2010
WO WO-2010124164 A1 10/2010
WO WO-2010129870 A1 11/2010
WO WO-2010144705 A1 12/2010
WO WO-2010148103 A1 12/2010
WO WO-2010150223 A1 12/2010
WO WO-2011018458 A1 2/2011
WO WO-2011019797 A3 2/2011
WO WO-2011041398 A1 4/2011
WO WO-2011060536 A1 5/2011
WO WO-2011063231 A1 5/2011
WO WO-2011080260 A1 7/2011
WO WO-2011106711 A1 9/2011
WO WO-2011109260 A1 9/2011
WO WO-2011110374 A1 9/2011
WO WO-2011117644 A2 9/2011
WO WO-2012006444 A2 1/2012
WO WO-2012033821 A1 3/2012
WO WO-2012058344 A1 5/2012
WO WO-2012058349 A4 5/2012
WO WO-2012058353 A4 5/2012
WO WO-2012058355 A4 5/2012
WO WO-2012061042 A1 5/2012
WO WO-2012116206 A1 8/2012
WO WO-2012141790 A1 10/2012
WO WO-2012158917 A1 11/2012
WO WO-2012173929 A1 12/2012
WO WO-2012174008 A1 12/2012
WO WO-2013126416 A1 8/2013
WO WO-2013170872 A1 11/2013
WO WO-2014019712 A1 2/2014
WO WO-2015084831 A1 6/2015

OTHER PUBLICATIONS

"U.S. Appl. No. 12/255,945, Advisory Action dated Feb. 10, 2012", 3 pgs.
"U.S. Appl. No. 12/255,945, Advisory Action dated Mar. 27, 2014", 3 pgs.
"U.S. Appl. No. 12/255,945, Examiner Interview Summary dated Aug. 13, 2013", 3 pgs.
"U.S. Appl. No. 12/255,945, Examiner Interview Summary dated Sep. 22, 2011", 3 pgs.
"U.S. Appl. No. 12/255,945, Examiner's Answer dated Feb. 12, 2015", 26 pgs.
"U.S. Appl. No. 12/255,945, Final Office Action dated Sep. 30, 2013", 21 pgs.
"U.S. Appl. No. 12/255,945, Final Office Action dated Nov. 28, 2011", 14 pgs.
"U.S. Appl. No. 12/255,945, Non Final Office Action dated May 7, 2013", 23 pgs.

(56) References Cited

OTHER PUBLICATIONS

"U.S. Appl. No. 12/255,945, Non Final Office Action dated Jul. 24, 2014", 26 pgs.
"U.S. Appl. No. 12/255,945, Non Final Office Action dated Aug. 4, 2011", 12 pgs.
"U.S. Appl. No. 12/255,945, Restriction Requirement dated Jun. 7, 2011", 8 pgs.
"U.S. Appl. No. 12/371,096, Final Office Action dated Jul. 6, 2011", 23 pgs.
"U.S. Appl. No. 12/371,096, Non Final Office Action dated Mar. 30, 2011", 19 pgs.
"U.S. Appl. No. 12/371,096, Non Final Office Action dated Apr. 17, 2014", 23 pgs.
"U.S. Appl. No. 12/371,096, Non Final Office Action dated Aug. 28, 2014", 21 pgs.
"U.S. Appl. No. 12/571,969, Advisory Action dated Oct. 21, 2013", 3 pgs.
"U.S. Appl. No. 12/571,969, Examiner Interview Summary dated Feb. 26, 2015", 3 pgs.
"U.S. Appl. No. 12/571,969, Examiner Interview Summary dated Mar. 11, 2013", 3 pgs.
"U.S. Appl. No. 12/571,969, Final Office Action dated Jan. 15, 2015", 9 pgs.
"U.S. Appl. No. 12/571,969, Final Office Action dated Jul. 31, 2013", 8 pgs.
"U.S. Appl. No. 12/571,969, Non Final Office Action dated Jun. 26, 2014", 8 pgs.
"U.S. Appl. No. 12/571,969, Non Final Office Action dated Dec. 19, 2012", 7 pgs.
"U.S. Appl. No. 12/571,969, Notice of Allowance dated Jun. 23, 2015", 8 pgs.
"U.S. Appl. No. 12/571,969, Preliminary Amendment filed Mar. 16, 2010", 3 pgs.
"U.S. Appl. No. 12/571,969, Response filed Mar. 6, 2013 to Non Final Office Action dated Dec. 19, 2012", 10 pgs.
"U.S. Appl. No. 12/571,969, Response filed May 15, 2015 to Final Office Action dated Jan. 15, 2015", 16 pgs.
"U.S. Appl. No. 12/571,969, Response filed Jun. 4, 2012 to Restriction Requirement dated May 9, 2012", 9 pgs.
"U.S. Appl. No. 12/571,969, Response filed Sep. 26, 2014 to Non Final Office Action dated Jun. 26, 2014", 12 pgs.
"U.S. Appl. No. 12/571,969, Response filed Sep. 30, 2013 to Final Office Action dated Jul. 31, 2013", 13 pgs.
"U.S. Appl. No. 12/571,969, Restriction Requirement dated May 9, 2012", 9 pgs.
"U.S. Appl. No. 12/893,306, Examiner Interview Summary dated Dec. 18, 2014", 3 pgs.
"U.S. Appl. No. 12/893,306, Final Office Action dated Sep. 11, 2014", 8 pgs.
"U.S. Appl. No. 12/893,306, Non Final Office Action dated Feb. 26, 2014", 9 pgs.
"U.S. Appl. No. 12/893,306, Notice of Allowability dated Jul. 29, 2015", 2 pgs.
"U.S. Appl. No. 12/893,306, Notice of Allowance dated Apr. 14, 2015", 5 pgs.
"U.S. Appl. No. 12/893,306, Response filed Jan. 12, 2015 to Final Office Action dated Sep. 11, 2014", 14 pgs.
"U.S. Appl. No. 12/893,306, Response filed May 22, 2014 to Non Final Office Action dated Feb. 26, 2014", 8 pgs.
"U.S. Appl. No. 12/893,306, Response filed Nov. 4, 2013 to Restriction Requirement dated Oct. 4, 2013", 11 pgs.
"U.S. Appl. No. 12/893,306, Restriction Requirement dated Oct. 4, 2013", 11 pgs.
"U.S. Appl. No. 12/938,905, Advisory Action dated Feb. 4, 2013", 3 pgs.
"U.S. Appl. No. 12/938,905, Appeal Decision dated Dec. 14, 2015", 18 pgs.
"U.S. Appl. No. 12/938,905, Examiner Interview Summary dated Jan. 30, 2013", 3 pgs.
"U.S. Appl. No. 12/938,905, Examiner Interview Summary dated Jul. 13, 2012", 3 pgs.
"U.S. Appl. No. 12/938,905, Examiner's Answer to Appeal Brief dated Jun. 24, 2013", 8 pgs.
"U.S. Appl. No. 12/938,905, Final Office Action dated Nov. 28, 2012", 11 pgs.
"U.S. Appl. No. 12/938,905, Non Final Office Action dated Jun. 4, 2012", 11 pgs.
"U.S. Appl. No. 12/938,905, Restriction Requirement dated Apr. 17, 2012", 8 pgs.
"U.S. Appl. No. 12/938,905, Restriction Requirement dated Sep. 14, 2012", 6 pgs.
"U.S. Appl. No. 12/938,913, Advisory Action dated Jan. 15, 2015", 3 pgs.
"U.S. Appl. No. 12/938,913, Examiner Interview Summary dated Dec. 18, 2014", 3 pgs.
"U.S. Appl. No. 12/938,913, Final Office Action dated Oct. 1, 2014", 9 pgs.
"U.S. Appl. No. 12/938,913, Non Final Office Action dated Mar. 11, 2014", 10 pgs.
"U.S. Appl. No. 12/938,913, Non Final Office Action dated Apr. 9, 2015", 8 pgs.
"U.S. Appl. No. 12/938,913, Notice of Allowance dated Nov. 12, 2015", 5 pgs.
"U.S. Appl. No. 12/938,913, Response filed Jan. 2, 2015 to Final Office Action dated Oct. 1, 2014", 10 pgs.
"U.S. Appl. No. 12/938,913, Response filed Feb. 2, 2015 to Advisory Action dated Jan. 15, 2015", 14 pgs.
"U.S. Appl. No. 12/938,913, Response filed Jun. 11, 2014 to Non Final Office Action dated Mar. 11, 2014", 9 pgs.
"U.S. Appl. No. 12/938,913, Response filed Jul. 7, 2015 to Non Final Office Action dated Apr. 9, 2015", 11 pgs.
"U.S. Appl. No. 12/938,913, Response filed Nov. 6, 2013 to Restriction Requirement dated Oct. 7, 2013", 1 pg.
"U.S. Appl. No. 12/938,913, Restriction Requirement dated Oct. 7, 2013", 7 pgs.
"U.S. Appl. No. 12/973,214, Examiner Interview Summary dated Jan. 24, 2014", 3 pgs.
"U.S. Appl. No. 12/973,214, Final Office Action dated Sep. 9, 2015", 10 pgs.
"U.S. Appl. No. 12/973,214, Final Office Action dated Nov. 21, 2013", 14 pgs.
"U.S. Appl. No. 12/973,214, Non Final Office Action dated Feb. 3, 2015", 14 pgs.
"U.S. Appl. No. 12/973,214, Non Final Office Action dated May 22, 2013", 11 pgs.
"U.S. Appl. No. 12/973,214, Response filed Nov. 6, 2015 to Final Office Action dated Sep. 9, 2015", 14 pgs.
"U.S. Appl. No. 12/973,214, Restriction Requirement dated Mar. 13, 2013", 8 pgs.
"U.S. Appl. No. 13/041,469, Non Final Office Action dated Mar. 22, 2013", 12 pgs.
"U.S. Appl. No. 13/041,469, Notice of Allowance dated Aug. 8, 2013", 6 pgs.
"U.S. Appl. No. 13/041,469, Notice of Allowance dated Oct. 3, 2013", 2 pgs.
"U.S. Appl. No. 13/041,469, Notice of Allowance dated Nov. 19, 2013", 2 pgs.
"U.S. Appl. No. 13/041,469, Response filed Jun. 18, 2013 to Non Final Office Action dated Mar. 22, 2013", 15 pgs.
"U.S. Appl. No. 13/041,469, Response filed Oct. 25, 2012 to Restriction Requirement dated Sep. 25, 2012", 1 pg.
"U.S. Appl. No. 13/041,469, Restriction Requirement dated Sep. 25, 2012", 5 pgs.
"U.S. Appl. No. 13/041,495, Appeal Brief filed Oct. 4, 2013", 39 pgs.
"U.S. Appl. No. 13/041,495, Examiner Interview Summary dated Feb. 20, 2013", 3 pgs.
"U.S. Appl. No. 13/041,495, Examiner interview Summary dated Aug. 6, 2013", 3 pgs.
"U.S. Appl. No. 13/041,495, Final Office Action dated Jun. 18, 2013", 14 pgs.

(56) References Cited

OTHER PUBLICATIONS

"U.S. Appl. No. 13/041,495, Non Final Office Action dated Nov. 2, 2012", 10 pgs.
"U.S. Appl. No. 13/041,495, Non Final Office Action dated Dec. 31, 2013", 11 pgs.
"U.S. Appl. No. 13/041,495, Notice of Allowance dated Jun. 11, 2014", 5 pgs.
"U.S. Appl. No. 13/041,495, Response filed Jan. 31, 2013 to Non Final Office Action dated Nov. 2, 2012", 13 pgs.
"U.S. Appl. No. 13/041,495, Response filed Mar. 31, 2014 to Non Final Office Action dated Dec. 31, 2013", 12 pgs.
"U.S. Appl. No. 13/041,495, Response filed Oct. 8, 2012 to Restriction Requirement dated Sep. 25, 2012", 8 pgs.
"U.S. Appl. No. 13/041,495, Restriction Requirement dated Sep. 25, 2012", 7 pgs.
"U.S. Appl. No. 13/041,495, Supplemental Amendment filed Feb. 20, 2013", 15 pgs.
"U.S. Appl. No. 13/041,665, Examiner Interview Summary dated Apr. 30, 2013", 3 pgs.
"U.S. Appl. No. 13/041,665, Final Office Action dated Mar. 5, 2013", 10 pgs.
"U.S. Appl. No. 13/041,665, Non Final Office Action dated Sep. 27, 2012", 10 pgs.
"U.S. Appl. No. 13/041,665, Notice of Allowance dated May 16, 2013", 7 pgs.
"U.S. Appl. No. 13/041,665, Response filed May 3, 2013 to Final Office Action dated Mar. 5, 2013", 13 pgs.
"U.S. Appl. No. 13/041,665, Response filed Sep. 17, 2012 to Restriction Requirement dated Aug. 20, 2012", 6 pgs.
"U.S. Appl. No. 13/041,665, Response filed Dec. 27, 2012 to Non Final Office Action dated Sep. 27, 2012", 16 pgs.
"U.S. Appl. No. 13/041,665, Restriction Requirement dated Aug. 20, 2012", 9 pgs.
"U.S. Appl. No. 13/041,883, Examiner Interview Summary dated Oct. 27, 2014", 3 pgs.
"U.S. Appl. No. 13/041,883, Final Office Action dated Jan. 15, 2015", 10 pgs.
"U.S. Appl. No. 13/041,883, Non Final Office Action dated Jun. 26, 2014", 8 pgs.
"U.S. Appl. No. 13/041,883, Non Final Office Action dated Aug. 13, 2015", 10 pgs.
"U.S. Appl. No. 13/041,883, Response filed Feb. 17, 2014 to Restriction Requirement dated Jan. 15, 2014", 3 pgs.
"U.S. Appl. No. 13/041,883, Response filed May 15, 2015 to Final Office Action dated Jan. 15, 2015", 13 pgs.
"U.S. Appl. No. 13/041,883, Response filed Sep. 26, 2014 to Non Final Office Action dated Jun. 26, 2014", 12 pgs.
"U.S. Appl. No. 13/041,883, Response filed Nov. 6, 2015 to Non Final Office Action dated Aug. 13, 2015", 16 pgs.
"U.S. Appl. No. 13/041,883, Restriction Requirement dated Jan. 15, 2014", 9 pgs.
"U.S. Appl. No. 13/045,169, Applicant's Summary of Examiner Interview filed Sep. 21, 2015", 2 pgs.
"U.S. Appl. No. 13/045,169, Examiner Interview Summary dated Sep. 10, 2015", 3 pgs.
"U.S. Appl. No. 13/045,169, Final Office Action dated Dec. 3, 2015", 8 pgs.
"U.S. Appl. No. 13/045,169, Non Final Office Action dated Jun. 4, 2015", 8 pgs.
"U.S. Appl. No. 13/045,169, Non Final Office Action dated Sep. 24, 2014", 9 pgs.
"U.S. Appl. No. 13/045,169, Response filed May 15, 2014 to Restriction Requirement dated Mar. 14, 2014", 10 pgs.
"U.S. Appl. No. 13/045,169, Response filed Aug. 31, 2015 to Non Final Office Action dated Jun. 4, 2015", 14 pgs.
"U.S. Appl. No. 13/045,169, Response filed Dec. 23, 2014 to Non Final Office Action dated Sep. 24, 2014", 10 pgs.
"U.S. Appl. No. 13/045,169, Restriction Requirement dated Mar. 14, 2014", 10 pgs.
"U.S. Appl. No. 13/047,924, Examiner Interview Summary dated Jan. 21, 2015", 3 pgs.
"U.S. Appl. No. 13/047,924, Examiner Interview Summary dated Jan. 25, 2013", 3 pgs.
"U.S. Appl. No. 13/047,924, Examiner interview Summary dated Sep. 5, 2013", 3 pgs.
"U.S. Appl. No. 13/047,924, Examiner Intervievil Summary dated Sep. 18, 2012", 3 pgs.
"U.S. Appl. No. 13/047,924, Final Office Action dated Apr. 3, 2015", 16 pgs.
"U.S. Appl. No. 13/047,924, Final Office Action dated Jul. 18, 2013", 14 pgs.
"U.S. Appl. No. 13/047,924, Non Final Office Action dated Sep. 21, 2012", 11 pgs.
"U.S. Appl. No. 13/047,924, Non Final Office Action dated Nov. 3, 2014", 14 pgs.
"U.S. Appl. No. 13/047,924, Response filed Feb. 3, 2015 to Non Final Office Action dated Nov. 3, 2014", 16 pgs.
"U.S. Appl. No. 13/047,924, Response filed May 1, 2013 to Restriction Requirement dated Apr. 1, 2013", 11 pgs.
"U.S. Appl. No. 13/047,924, Response filed Sep. 17, 2012 to Restriction Requirement dated Aug. 20, 2012", 9 pgs.
"U.S. Appl. No. 13/047,924, Response filed Oct. 18, 2013 to Final Office Action dated Jul. 18, 2013", 18 pgs.
"U.S. Appl. No. 13/047,924, Response filed Dec. 20, 2012 to Non Final Office Action dated Sep. 21, 2012", 19 pgs.
"U.S. Appl. No. 13/047,924, Restriction Requirement dated Apr. 1, 2013", 7 pgs.
"U.S. Appl. No. 13/047,924, Restriction Requirement dated Aug. 20, 2012", 8 pgs.
"U.S. Appl. No. 13/088,787, Response filed Aug. 20, 2015 to Final Office Action dated May 20, 2015", 9 pgs.
"U.S. Appl. No. 13/106,295, Non Final Office Action dated Jan. 24, 2013", 14 pgs.
"U.S. Appl. No. 13/106,295, Notice of Allowance dated Aug. 1, 2013", 9 pgs.
"U.S. Appl. No. 13/106,295, Response filed Apr. 16, 2013 to Non Final Office Action dated Jan. 24, 2013", 10 pgs.
"U.S. Appl. No. 13/106,295, Response filed Dec. 20, 2012 to Restriction Requirement dated Nov. 23, 2012", 1 pg.
"U.S. Appl. No. 13/106,295, Restriction Requirement dated Nov. 23, 2012", 5 pgs.
"U.S. Appl. No. 13/400,652, Non Final Office Action dated Jun. 17, 2015", 7 pgs.
"U.S. Appl. No. 13/400,652, Response filed Jan. 28, 2015 to Restriction Requirement dated Nov. 28, 2014", 17 pgs.
"U.S. Appl. No. 13/400,652, Response filed Apr. 13, 2015 to Restriction Requirement dated Feb. 13, 2015", 16 pgs.
"U.S. Appl. No. 13/400,652, Response filed Aug. 13, 2014 to Restriction Requirement dated Jun. 13, 2014", 19 pgs.
"U.S. Appl. No. 13/400,652, Response filed Sep. 16, 2015 to Non Final Office Action dated Jun. 17, 2015", 12 pgs.
"U.S. Appl. No. 13/400,652, Restriction Requirement dated Feb. 13, 2015", 8 pgs.
"U.S. Appl. No. 13/400,652, Restriction Requirement dated Jun. 13, 2014", 9 pgs.
"U.S. Appl. No. 13/400,652, Restriction Requirement dated Nov. 28, 2014", 7 pgs.
"U.S. Appl. No. 13/527,981, Final Office Action dated Feb. 5, 2015", 22 pgs.
"U.S. Appl. No. 13/527,981, Final Office Action dated Nov. 6, 2015", 13 pgs.
"U.S. Appl. No. 13/527,981, Non Final Office Action dated Feb. 26, 2015", 10 pgs.
"U.S. Appl. No. 13/527,981, Non Final Office Action dated Sep. 15, 2014", 19 pgs.
"U.S. Appl. No. 13/527,981, Response filed May 27, 2014 to Restriction Requirement dated Mar. 27, 2014", 11 pgs.
"U.S. Appl. No. 13/527,981, Response filed Jul. 27, 2015 to Non-Final Office Action dated Feb. 26, 2015", 25 pgs.
"U.S. Appl. No. 13/527,981, Restriction Requirement dated Mar. 27, 2014", 7 pgs.

(56) References Cited

OTHER PUBLICATIONS

"U.S. Appl. No. 13/674,531, Final Office Action dated Apr. 29, 2015", 8 pgs.
"U.S. Appl. No. 13/674,531, Response filed Jul. 29, 2015 to Final Office Action dated Apr. 29, 2015", 12 pgs.
"U.S. Appl. No. 13/674,531, Restriction Requirement dated Sep. 24, 2014", 7 pgs.
"U.S. Appl. No. 13/713,710, Notice of Allowance dated Sep. 15, 2015", 10 pgs.
"U.S. Appl. No. 13/713,710, Response filed Aug. 25, 2015 to Restriction Requirement dated Jul. 2, 2015", 7 pgs.
"U.S. Appl. No. 13/713,710, Restriction Requirement dated Jul. 2, 2015", 6 pgs.
"U.S. Appl. No. 13/766,419, Advisory Action dated May 18, 2015" 2 pgs.
"U.S. Appl. No. 13/766,419, Final Office Action dated Jan. 13, 2015", 16 pgs.
"U.S. Appl. No. 13/766,419, Non Final Office Action dated Sep. 5, 2014", 14 pgs.
"U.S. Appl. No. 13/766,419, Response filed May 12, 2015 to Final Office Action dated Jan. 13, 2015", 13 pgs.
"U.S. Appl. No. 13/766,419, Response filed Dec. 5, 2014 to Non Final Office Action dated Sep. 5, 2014", 12 pgs.
"U.S. Appl. No. 13/800,334, Examiner Interview Summary dated Jan. 29, 2015", 4 pgs.
"U.S. Appl. No. 13/800,334, Final Office Action dated Feb. 12, 2015", 11 pgs.
"U.S. Appl. No. 13/800,334, Non Final Office Action dated Sep. 24, 2015", 14 pgs.
"U.S. Appl. No. 13/800,334, Non Final Office Action dated Oct. 22, 2014", 11 pgs.
"U.S. Appl. No. 13/800,334, Response filed Jan. 21, 2015 to Non Final Office Action dated Oct. 22, 2014", 12 pgs.
"U.S. Appl. No. 13/800,334, Response filed Jul. 10, 2015 to Final Office Action dated Feb. 12, 2015", 8 pgs.
"U.S. Appl. No. 13/800,334, Response filed Dec. 16, 2015 to Non Final Office Action dated Sep. 24, 2015", 16 pgs.
"U.S. Appl. No. 14/027,340, Advisory Action dated Sep. 17, 2015", 3 pgs.
"U.S. Appl. No. 14/027,340, Final Office Action dated Jul. 8, 2015", 10 pgs.
"U.S. Appl. No. 14/027,340, Non Final Office Action dated Jan. 22, 2015", 11 pgs.
"U.S. Appl. No. 14/027,340, Non Final Office Action dated Dec. 9, 2015", 10 pgs.
"U.S. Appl. No. 14/027,340, Response filed May 21, 2015 to Non Final Office Action dated Jan. 22, 2015", 14 pgs.
"U.S. Appl. No. 14/027,340, Response filed Sep. 9, 2015 to Final Office Action dated Jul. 8, 2015", 15 pgs.
"U.S. Appl. No. 14/064,970, Final Office Action dated Oct. 19, 2015", 10 pgs.
"U.S. Appl. No. 14/064,970, Non Final Office Action dated Mar. 12, 2015", 11 pgs.
"U.S. Appl. No. 14/064,970, Response filed Jul. 8, 2015 to Non Final Office Action dated Mar. 12, 2015", 8 pgs.
"U.S. Appl. No. 14/064,970, Response filed Dec. 9, 2014 to Restriction Requirement dated Oct. 9, 2014", 11 pgs.
"U.S. Appl. No. 14/064,970, Response filed Dec. 15, 2015 to Final Office Action dated Oct. 19, 2015", 11 pgs.
"U.S. Appl. No. 14/064,970, Restriction Requirement dated Oct. 9, 2014", 9 pgs.
"U.S. Appl. No. 14/105,669, Response filed Oct. 13, 2015 to Restriction Requirement dated Sep. 8, 2015", 7 pgs.
"U.S. Appl. No. 14/105,669, Restriction Requirement dated Sep. 8, 2015", 6 pgs.
"U.S. Appl. No. 14/107,316, Response filed Dec. 16, 2015 to Restriction Requirement dated Oct. 29, 2015", 8 pgs.
"U.S. Appl. No. 14/107,316, Restriction Requirement dated Oct. 29, 2015", 8 pgs.
"U.S. Appl. No. 14/159,071, Final Office Action dated May 14, 2015", 7 pgs.
"U.S. Appl. No. 14/159,071, Non Final Office Action dated Dec. 8, 2014", 14 pgs.
"U.S. Appl. No. 14/483,214, Non Final Office Action dated Jun. 5, 2015", 8 pgs.
"U.S. Appl. No. 14/483,214, Response filed May 15, 2015 to Restriction Requirement dated Mar. 25, 2015", 2 pgs.
"U.S. Appl. No. 14/483,214, Response filed Sep. 2, 2015 to Non Final Office Action dated Jun. 5, 2015", 13 pgs.
"U.S. Appl. No. 14/483,214, Restriction Requirement dated Mar. 25, 2015", 6 pgs.
"U.S. Appl. No. 14/812,583, Preliminary Amendment filed Jul. 29, 2015", 6 pgs.
"U.S. Appl. No. 14/865,762, Preliminary Amendment filed Oct. 14, 2015", 6 pgs.
"U.S. Appl. No. 14/973,057, Preliminary Amendment filed Dec. 18, 2015", 7 pgs.
"Australian Application Serial No. 2013222609, Response flied Sep. 17, 2015 to First Examiner Report dated Feb. 16, 2015", 17 pgs.
"European Application Serial No. 07809326.7, Office Action dated Jan. 28, 2009", 2 pgs.
"European Application Serial No. 07809326.7, Response filed Jun. 6, 2012 to Extended European Search Report dated Nov. 15, 2011", 6 pgs.
"European Application Serial No. 09792468.2, Examination Notification Art. 94(3) dated Jan. 29, 2015", 5 pgs.
"European Application Serial No. 12156937.0, Decision of Grant dated May 4, 2015", 2 pgs.
"European Application Serial No. 12156937.0, Examination Notification Art. 94(3) dated Dec. 11, 2013", 5 pgs.
"European Application Serial No. 12156937.0, Extended European Search Report dated Sep. 6, 2012", 9 pgs.
"European Application Serial No. 12156937.0, Response filed Apr. 16, 2013 to Extended European Search Report dated Sep. 6, 2012", 9 pgs.
"European Application Serial No. 12156937.0, Response filed Apr. 17, 2014 to Examination Notification Art. 94(3) dated Dec. 11, 2013", 15 pgs.
"European Application Serial No. 13710642.3, Office Action dated Oct. 10, 2014", 2 pgs.
"International Application Serial No. PCT/US2009/056670, Invitation to Pay Additional Fees and Partial Search Report dated Nov. 26, 2009".
"International Application Serial No. PCT/US2010/038845, International Preliminary Report on Patentability dated Jan. 5, 2012", 9 pgs.
"International Application Serial No. PCT/US2011/026333, Invitation to Pay Additional Fees dated May 3, 2011".
"International Application Serial No. PCT/US2012/060848, Invitation to Pay Additional Fees dated Feb. 6, 2013".
"International Application Serial No. PCT/US2013/067505, International Preliminary Report on Patentability dated May 14, 2015", 13 pgs.
"International Application Serial No. PCT/US2013/067505, Invitation to Pay Additional Fees dated Feb. 6, 2014", 6 pgs.
"International Application Serial No. PCT/US2015/039561, International Search Report dated Sep. 14, 2015", 5 pgs.
"International Application Serial No. PCT/US2015/039561, Written Opinion dated Sep. 14, 2015", 6 pgs.
"Japanese Application Serial No. 2014-257600, Office Action dated Oct. 27, 2015", (W/ English Translation), 6 pgs.
"Japanese Application Serial No. 2014-511538, Office Action dated Nov. 17, 2015", W/ English Translation, 5 pgs.
"Japanese Application Serial No. 2014-558800, Office Action dated Sep. 1, 2015", (W/ English Translation), 8 pgs.
"MAX-Ti™ Modular Protrusio Cage", Surgical Technique brochure. Biomet Orthopedics, Inc., (2003), 10 pgs.
"MAX-Ti™ Modular Protrusio Cage", Surgical Technique brochure. Biomet Orthopedics, Inc., (2006), 12 pgs.
"OSS™ Orthopaedic Salvage System, Femoral/Tibial Augmentation", Biomet Orthopedics, Inc.,, (2003), 1-8.

(56) References Cited

OTHER PUBLICATIONS

"PAR 5™ Protrusio Acetabular Reconstruction System", Biomet Orthopedics, Inc., (2006), 12 pgs.
"Patient Matched PMI Implants, C.A.M.R.A. 3-D Imaging", Brochure, Biomet, Inc., Form Y-BMI-191/013191, (1991), 6 pgs.
"Regenerex® Tibial Cone Augment, Surgical Technique Addendum to the Vanguard® SSK Revision System", brochure. Biomet® Orthopedics., (2010), 1-8.
"Signature™ Personalized Patient Care, Surgical Technique Addendum to the Vanguard Knee System", brochure. Biomet® Orthopedics, Inc., (2009), 1-8.
"Taperloc Complete Hip System Surgical Technique", Biomet: Brochure 2012 REV061512, (2011), 12 pgS.
"TruMatch™ Personalized knee replacement solutions", SIGMA® DePuy Orthopaedics, Inc., (2009), 2 pgs.
"United Kingdom Application Serial No. 1207103.1, Amendment filed Apr. 13, 2012", 9 pgs.
"United Kingdom Application Serial No. 1207103.1, Response filed Sep. 14, 2015 to Office Action dated May 14, 2015", 22 pgs.
"United Kingdom Application Serial No. 1216577.5, Office Action dated Oct. 29, 2015", 4 pgs.
"United Kingdom Application Serial No. 1516672.1, Combined Search and Examination Report dated Oct. 22, 2015", 5 pgs.
BIOMET, "The Oxford® Partial Knee System Surgical Technique", Biomet: Manual of the Surgical Technique, (Feb. 2010), 44 pgs.
Schuller-Gotzburg, P, et al., "3D-Implantatplanung und Stereolithographie-implantatbohrschablonen", Stomatologie 101.3, (May 2004), 55-59.
Subburaj, K, et al., "Automated 3D Geometric Reasoning in Computer Assisted Joint Reconstructive Surgery", IEEE International Conference on Automation Science and Engineering, (2009), 367-372.
Thoma, W, "Endoprosthetic care of the knee joint based on a 3D computer chromatography subtraction process", Topic: Computer-aided orthopedic surgery. Orthopedist 2000 29: Springer Verlag W/ Original German Document, (2000), 641-644.
"U.S. Appl. No. 14/798,809, Examiner Interview Summary dated Sep. 14, 2017", 3 pgs.
"U.S. Appl. No. 14/798,809, Non Final Office Action dated Jun. 28, 2017", 7 pgs.
"U.S. Appl. No. 14/798,809, Response filed Apr. 3, 2017 to Restriction Requirement dated Jan. 4, 2017", 8 pgs.
"U.S. Appl. No. 14/798,809, Response filed Sep. 26, 2017 to Non Final Office Action dated Jun. 28, 2017", 9 pgs.
"U.S. Appl. No. 14/798,809, Restriction Requirement dated Jan. 4, 2017", 10 pgs.
U.S. Appl. No. 12/893,306, U.S. Pat. No. 9,113,971, filed Sep. 29, 2010, Femoral Acetabular Impingement Guide.
U.S. Appl. No. 14,798,809, filed Jul. 14, 2015, Femoral Acetabular Impingement Guide.
U.S. Appl. No. 13/088,787, filed Apr. 18, 2011, Patient-Specific Guide for Partial Acetuabular Socket Replacement.
"3D-Implantatplanung und StereolithographieImplantatbohrschablonen", Stomatologie 101.3, (2004), 55-59.
"Amazing Precision. Beautiful Results. The next evolution of MAKOplasty® is here", MAKO Surgical Corp., (Feb. 2009), 6 pgs.
"U.S. Appl. No. 13/088,787, Final Office Action dated May 20, 2015", 11 pgs.
"U.S. Appl. No. 13/088,787, Non Final Office Action dated Sep. 11, 2014", 8 pgs.
"U.S. Appl. No. 13/088,787, Notice of Allowance dated Oct. 21, 2015", 6 pgs.
"U.S. Appl. No. 13/088,787, Response filed May 12, 2014 to Restriction Requirement dated Mar. 12, 2014", 10 pgs.
"U.S. Appl. No. 13/088,787, Response filed Dec. 10, 2014 to Non Final Office Action dated Sep. 11, 2014", 11 pgs.
"U.S. Appl. No. 13/088,787, Restriction Requirement dated Mar. 12, 2014", 9 pgs.
"Ascent Total Knee System", Biomet, Inc., (1999), 16 pgs.
"Australian Application Serial No. 2013222609, First Examiner Report dated Feb. 16, 2015", 5 pgs.
"Comprehensive® Reverse Shoulder System", Biomet Orthopedics brochure, (2009), 8 pgs.
"Comprehensive® Reverse Shoulder System Surgical Technique", Biomet Orthopedics, (2009-2012), 48 pgs.
"Comprehensive® Reverse Shoulder System Technical Design Features", Biomet Orthopedics, (2009), 3 pgs.
"Comprehensive® Shoulder System Surgical Technique", Biomet Orthopedics brochure, (2007), 1-53.
"Comprehensive® Total Shoulder System", Biomet Orthopedics brochure, (2011), 4 pgs.
"Customized Patient Instruments, Patient specific instruments for patient specific needs", DePuy Orthopaedics, Inc., (2008), 14 pgs.
"Customized Patient Instruments, Primary Cruciate Retaining Surgical Technique for use with the Sigma® Knee System Utilizing Specialist® 2 Instrumentation", DePuy Orthopaedics, Inc., (2008), 1-23.
"Discovery® Elbow System", Biomet Orthopedics, Inc., (Nov. 30, 2007), 3 pgs.
"Discovery® Elbow System Surgical Technique", Biomet Orthopedics, Inc., (Dec. 31, 2008), 1-25.
"European Application Serial No. 07809326.7, Examination Notification Art, 94(3) dated Jan. 22, 2015", 6 pgs.
"European Application Serial No. 07809326.7, Extended European Search Report dated Nov. 15, 2011", 6 pgs.
"European Application Serial No. 09731923.0, Examination Notification Art. 94(3) dated Feb. 10, 2015", 7 pgs.
"European Application Serial No. 10705064.3, Examination Notification Art. 94(3) dated Feb. 4, 2015", 6 pgs.
"European Application Serial No. 12724475.4, Examination Notification Art. 94(3) dated Nov. 24, 2014", 7 pgs.
"Great Britain Application Serial No. 1116054.6, Search Report dated Dec. 21, 2011", 4 pgs.
"Hipsextant Instructions of Use", Surgical Planning Associates, Inc., (2011), 19 pgs.
"International Application Serial No. PCT/EP2010/061630, International Search Report dated Nov. 30, 2010", 3 pgs.
"International Application Serial No. PCT/US2007/013223, International Preliminary Report on Patentability dated Dec. 24, 2008", 5 pgs.
"International Application Serial No. PCT/US2007/013223, International Search Report dated Nov. 26, 2007", 3 pgs.
"International Application Serial No. PCT/US2007/013223, Written Opinion dated Nov. 26, 2007", 4 pgs.
"International Application Serial No. PCT/US2009/039507, International Preliminary Report on Patentability dated Oct. 28, 2010", 9 pgs.
"International Application Serial No. PCT/US2009/039507, International Search Report dated Jul. 14, 2009", 6 pgs.
"International Application Serial No. PCT/US2009/039507, Written Opinion dated Jul. 14, 2009", 7 pgs.
"International Application Serial No. PCT/US2009/039578, International Preliminary Report on Patentability dated Oct. 28, 2010", 9 pgs.
"International Application Serial No. PCT/US2009/039578, International Search Report dated Jul. 31, 2009", 6 pgs.
"International Application Serial No. PCT/US2009/039578, Written Opinion dated Jul. 31, 2008",7 pgs.
"International Application Serial No. PCT/US2009/056670, International Preliminary Report on Patentability dated Mar. 31, 2011", 12 pgs.
"International Application Serial No. PCT/US2009/056670, International Search Report dated Mar. 2, 2010", 7 pgs.
"International Application Serial No. PCT/US2009/056670, Written Opinion dated Mar. 2, 2010", 10 pgs.
"International Application Serial No. PCT/US2010/024073, International Preliminary Report on Patentability dated Aug. 25, 2011", 8 pgs.
"International Application Serial No. PCT/US2010/024073, International Search Report dated Jun. 4, 2010", 4 pgs.
"International Application Serial No. PCT/US2010/024073, Written Opinion dated Jun. 4, 2010", 6 pgs.

(56) References Cited

OTHER PUBLICATIONS

"International Application Serial No. PCT/US2010/024579, International Preliminary Report on Patentability dated Sep. 1, 2011", 7 pgs.
"International Application Serial No. PCT/US2010/024579, International Search Report dated Apr. 22, 2010", 3 pgs.
"International Application Serial No. PCT/US2010/024579, Written Opinion dated Apr. 22, 2010", 5 pgs.
"International Application Serial No. PCT/US2010/024584, International Preliminary Report on Patentability dated Sep. 1, 2011", 8 pgs.
"International Application Serial No. PCT/US2010/024584, International Search Report dated Aug. 19, 2010", 6 pgs.
"International Application Serial No. PCT/US2010/024584, Written Opinion dated Aug. 19, 2010", 6 pgs.
"International Application Serial No. PCT/US2010/038177, International Preliminary Report on Patentability dated Dec. 22, 2011", 10 pgs.
"International Application Serial No. PCT/US2010/038177, International Search Report dated Aug. 24, 2010", 4 pgs.
"International Application Serial No. PCT/US2010/038177, Written Opinion dated Aug. 24, 2010", 8 pgs.
"International Application Serial No. PCT/US2010/038845, International Search Report dated Oct. 5, 2010", 4 pgs.
"International Application Serial No. PCT/US2010/038845, Written Opinion dated Oct. 5, 2010", 7 pgs.
"International Application Serial No. PCT/US2010/050701, International Preliminary Report on Patentability dated Apr. 12, 2012", 10 pgs.
"International Application Serial No. PCT/US2010/050701, International Search Report dated Dec. 7, 2010", 6 pgs.
"International Application Serial No. PCT/US2010/050701, Written Opinion dated Dec. 7, 2010", 8 pgs.
"International Application Serial No. PCT/US2011/026333, International Preliminary Report on Patentability dated Sep. 7, 2012", 10 pgs.
"International Application Serial No. PCT/US2011/026333, International Search Report dated Aug. 9, 2011", 6 pgs.
"International Application Serial No. PCT/US2011/026333, Written Opinion dated Aug. 9, 2011", 8 pgs.
"International Application Serial No. PCT/US2011/026412, International Search Report dated May 9, 2011", 5 pgs.
"International Application Serial No. PCT/US2011/026412, Written Opinion dated May 9, 2011", 6 pgs.
"International Application Serial No. PCT/US2011/057300, International Search Report dated Mar. 5, 2012", 7 pgs.
"International Application Serial No. PCT/US2011/057300, Written Opinion dated Mar. 5, 2012", 9 pgs.
"International Application Serial No. PCT/US2012/026356, International Preliminary Report on Patentability dated Sep. 6, 2013", 8 pgs.
"International Application Serial No. PCT/US2012/026356, International Search Report dated May 8, 2012", 5 pgs.
"International Application Serial No. PCT/US2012/026356, Written Opinion dated May 8, 2012", 6 pgs.
"International Application Serial No. PCT/US2012/038351, International Preliminary Report on Patentability dated Nov. 28, 2013", 9 pgs.
"International Application Serial No. PCT/US2012/038351, Written Opinion dated Jul. 6, 2012", 8 pgs.
"International Application Serial No. PCT/US2012/041893, International Search Report dated Oct. 23, 2012", 5 pgs
"International Application Serial No. PCT/US2012/042081, International Preliminary Repolt on Patentability dated Jan. 3, 2014", 7 pgs.
"International Application Serial No. PCT/US2012/042081, Written Opinion dated Sep. 5, 2012", 6 pgs.
"International Application Serial No. PCT/US2012/052853, International Preliminary Report on Patentability dated Mar. 13, 2014", 13 pgs.
"International Application Serial No. PCT/US2012/05283, International Search Report dated Nov. 15, 2012", 6 pgs.
"International Application Serial No. PCT/US2012/052853, Written Opinion dated Nov. 15, 2012", 12 pgs.
"International Application Serial No. PCT/US2012/059189, International Preliminary Report on Patentability dated Apr. 24, 2014", 10 pgs.
"International Application Serial No. PCT/US2012/059189, International Search Report dated Dec. 18, 2012", 6 pgs.
"International Application Serial No. PCT/US2012/059189, Written Opinion dated Dec. 18, 2012", 9 pgs.
"International Application Serial No. PCT/US2012/060842, International Preliminary Report on Patentability dated May 8, 2014", 7 pgs.
"International Application Serial No. PCT/US2012/060842, International Search Report dated Feb. 6, 2013", 4 pgs.
"International Application Serial No. PCT/US2012/060842, Written Opinion dated Feb. 6, 2013", 5 pgs.
"International Application Serial No. PCT/US2012/060848, International Preliminary Report on Patentability dated May 8, 2014", 11 pgs.
"International Application Serial No. PCT/US2012/060848, International Search Report dated Apr. 12, 2013", 6 pgs.
"International Application Serial No. PCT/US2012/060848, Written Opinion dated Apr. 12, 2013", 9 pgs.
"International Application Serial No. PCT/US2012/060853, International Preliminary Report on Patentability dated May 8, 2014", 11 pgs.
"International Application Serial No. PCT/US2012/060853, Written Opinion dated Apr. 9, 2013", 9 pgs.
"International Application Serial No. PCT/US2012/060854, International Preliminary Report on Patentability dated May 8, 2014", 8 pgs.
"International Application Serial No. PCT/US2012/060854, International Search Report dated Feb. 6, 2013", 4 pgs.
"International Application Serial No. PCT/US2012/060854, Written Opinion dated Feb. 6, 2013", 6 pgs.
"International Application Serial No. PCT/US2013/026875, International Preliminary Report on Patentability dated Sep. 4, 2014", 9 pgs.
"International Application Serial No. PCT/US2013/026875, International Search Report dated Jun. 7, 2013", (Jun. 7, 2013), 5 pgs.
"International Application Serial No. PCT/US2013/026875, Written Opinion dated Jun. 7, 2013", 8 pgs.
"International Application Serial No. PCT/US2013/057097, International Preliminary Report on Patentability dated Mar. 12, 2015", 10 pgs.
"International Application Serial No. PCT/US2013/057097, International Search Report dated Oct. 14, 2013", 6 pgs.
"International Application Serial No. PCT/US2013/057097, Written Opinion dated Oct. 14, 2013", 9 pgs.
"International Application Serial No. PCT/US2013/067505, International Search Report dated Apr. 14, 2014", 5 pgs.
"International Application Serial No. PCT/US2013/067505, Written Opinion dated Apr. 14, 2014", 11 pgs.
"International Application Serial No. PCT/US2013/074288, International Preliminary Report of Patentability dated Jun. 25, 2015", 13 pgs.
"International Application Serial No. PCT/US2013/074288, International Search Report dated May 23, 2014", 7 pgs.
"International Application Serial No. PCT/US2013/074288, Written Opinion dated May 23, 2014", 11 pgs.
"International Application Serial No. PCT/US2014/022000, International Search Report dated Jun. 24, 2014", 3 pgs.
"International Application Serial No. PCT/US2014/022000, Written Opinion dated Jun. 24, 2014", 5 pgs.
"International Application Serial No. PCT/US2014/023655, International Search Report dated Jul. 10, 2014", 4 pgs.
"International Application Serial No. PCT/US2014/023655, Written Opinion dated Jul. 10, 2014", 6 pgs.
"International Application Serial No. PCT/US2014/068131, International Search Report dated May 8, 2015", 5 pgs.

(56) References Cited

OTHER PUBLICATIONS

"International Application Serial No. PCT/US2014/068131, Written Opinion dated May 8, 2015", 9 pgs.
"Is Subchondroplasty® Right for Me?", [Online] retrieved from the internet: <http://www.subchondroplast}'..com/about subchondroplast}'./ is subchondroplasty right for >, (Jul. 1, 2013), 1 pg.
"Japanese Application Serial No. 2014511538, Office Action dated Apr. 7, 2015", (W/ English Translation), 8 pgs.
"Knee tensor combined with laser femoral head locator", Research Disclosure, No. 507, (Jul. 2006), 903.
"Method for constructing an allograft sleeve", Research Disclosure, No. 476, (Dec. 2003), 1294 pgs.
"OSS™ Orthopaedic Salvage System, Femoral/Tibial Augmentation", Biomet Orthopedics, Inc.,, (Mar. 31, 2004), 1-8.
"Oxford® Partial Knee", Biomet, (Feb. 2011), 8 pgs.
"Oxford® Partial Knee Microplasty® Instrumentation Surgical Technique", Biomet, (May 2011), 1-54.
"Patient Matched PMI Implants, C.A.M.R.A. 3-D Imaging", Biomet, Inc., (Jan. 31, 1991), 6 pgs.
"Regenerex® Tibial Cone Augment, Surgical Technique Addendum to the Vanguard® SSK Revision System", Biomet® Orthopedics., (Mar. 31, 2010), 1-8.
"Signature™ Hip Technology Personalized Patient Care brochure", Biomet® Orthopedics., (2013), 8 pgs.
"Signature™ Personalized Patient Care", Surgical Technique Acetabular Guide System brochure, Biomet® Orthopedics, (2013), 1-13.
"Signature™ Personalized Patient Care, Surgical Technique Addendum to the Vanguard Knee System", Biomet® Orthopedics, Inc., (May 15, 2009), 1-8.
"Signature™ Personalized Patient Care, Surgical Technique Addendum Vanguard® Complete Knee System", Biomet® Orthopedics Brochure, (2011), 1-32.
"Subchandroplasty", [Online] retrieved from the internet: <http://www.subchondroplasty.com/>, (Jul. 1, 2013), 1 pg.
"The Oxford® Partial Knee Surgical Technique", Biomet, (Feb. 2010), 1-38.
"United Kingdom Application Serial No. 1207103.1, Office Action dated May 14, 2015", 3 pgs.
"Vanguard® PFR Partial Knee Patellofemoral Replacement System", Surgical Technique, Biomet Orthopaedics (Aug. 31, 2010), 1-25.
"What is Subchondroplasty", [Online]. Retrieved from the Internet: <http://www.subchondroplasty.com/about subchondroplasty/what is subchondroplasty.>, (Jul. 1, 2013), 2 pgs.
"Zimmer® UniSpacer® Knee System", Zimmer, Inc., (2005), 4 pgs.
Birnbaum, Klaus M. D, "Computer-Assisted Orthopedic Surgery With Individual Templates and Comparison to Conventional Method", SPINE vol. 26, No. 4. Lippincott Williams & Wilkins, Inc., (2001), 365-370.
Botha, Charl P, "Technical Report: DeVIDE—The Deift Visualisation and Image processing Development Environment", (May 31, 2006), 1-49.
Cohen, Zohara A, et al., "Knee cartilage topography, thickness, and contact areas from MRI: in-vitro calibration and in-vivo measurements", Journal of the OsteoArthritis Research Society International. Osteoarthritis and Cartilage, vol. 7; No. 1, (1999), 95-109.
Deakon, "Posterior Cruciate Ligament Reconstruction Technique Using the Modular ACL/PCL Guide Rationale and Surgical Technique", Arthrotek®, a Biomet Company, (2003), 6 pgs.
Eckhoff, Donald G, et al., "Three-Dimensional Mechanics, Kinematics, and Morphology of the Knee Viewed in Virtual Reality", The Journal of Bone & Joint Surgery, vol. 81, (Dec. 4, 2005), 71-80.
Farr, J, et al., "Anteromedial Tibial Tubercle Osteotomy (Fulkerson Osteotomy)", Re-print from V. Sanchis-Alfonso (ed), Anterior Knee Pain and patellar Instability, DOI: 10.1007/978-0-85729-507-1_40,© Springer-Verlag London Limited 2011, 9 pgs.
Farr, J, et al., "Surgical Technique for Anteromedialization of the Tibial Tubercle with the Tracker™ AMZ Guide System", Sports Medicine and Arthroscopy Review, vol. 2, No. 3, (1994), 12 pgs.
Fortin, Thomas, et al., "Precise Dental Implant Placement in Bone Using Surgical Guides in Conjunction with Medical Imaging Techniques", Journal of Oral Implantology, Clinical, vol. 26, No. 4, (2000), 300-303.
Friedman, R J, et al., "The Use of Computerized Tomography in the Measurement of Glenoid Version", Journal of Bone & Joint Surgery Am. (JBJS) 1992;74, (Aug. 1992), 1032-1037.
Haaker, R G, et al., "Minimal-invasive navigiert implantierte unikondylare Knieendoprothese", Orthopade 2006 35: Spinger Medizin Verlag, (Sep. 13, 2006), 1073-1079.
Hafez, M A, et al., "Computer-assisted Total Knee Arthroplasty Using Patient-specific Templating", Clinical Orthopaedics and Related Research, No. 444 Lippincott Williams & Wilkins, (2006), 184-192.
Hazan, Eric J, "Computer-Assisted Orthopaedic Surgery, A New Paradigm", Techniques in Orthopaedics® vol. 18, No. 2,, (2003), 221-229.
Hutmacher, Dietmar W, "Scaffolds in tissue engineering bone and cartilage", Biomaterials, 2000 Elsevier Science Ltd., (2000), 2529-2543.
Kaus, Michael R, "Automated Segmentation of MR Images of Brain Tumors", Radiology, vol. 218, No. 2 (2001), 586-591.
Kelly, Todd C, "Role of Navigation in Total Hip Arthroplasty", The Journal of Bone & Joint Surgery(2009) vol. 91-A, Supplement 1, (2009), 153-8.
Klein, M, "Robot assisted insertion of craniofacial implants—clinical experience", CARS 2001, Elsevier Science B.V., (2001), 133-138.
Lombardi, Adolph, et al., "Patient-Specific Approach in Total Knee Arthroplasty", Knee Orthopedics, ORTHOSuperSite, [Online]. Retrieved from the Internet: <http://www.orthosupersite.com/view.aspx?rid=31419,>, (Sep. 1, 2008), 5 pgs.
Lynch, John A, et al., "Cartilage segmentation of 3D MRI scans of the osteoarthritic knee combining user knowledge and active contours", Medical Imaging 2000: Image Processing SPIE vol. 3979, (2000), 925-935.
Murphy, S B, et al., "The Hip Sextant: Navigation of Acetabular Component Orientation Using a Mechanical Instrument", (2009), 1 pg.
Nicholls, Paul M. D, "Trauma Grand Rounds PMI (Patient-Matched Implants)", Biomet Orthopedics, Inc.,, (Feb. 29, 2000), 1 pg.
Overhoff, H M, et al., "Total Knee Arthroplasty: Coordinate System Definition and Planning based on 3-D Ultrasound Image Volumes", CARS 2001, Elsevier Science B.V., (2001), 283-288.
Portheine, F, "CT-basierte Planung and DISOS-Schablonennavigation in der Kniegelenkendoprothetik", Navigation and Robotic in der Gelenk—und Wirbelsaulenchiruqie, Kapitel 32, Springer Verlag, (2003), 262-269.
Portheine, F, et al., "Entwicklung eines klinischen Demonstrators fur die computerunterstutzte Orthopadische Chirurgie mit CT-Bildbasierten Individualschablonen, Bildverarbeitung fur die Medizin", English version: FIP ID 752773, (1998), 5 pgs.
Portheine, K, "Development of a clinical demonstrator for computer assisted orthopedic surgery with CT-image based individual templates", Computer Assisted Radiology and Surgery Elsevier Science B.V., English Version of FIP ID 752770, (1997), 944-949.
Radermacher, K, et al., "Computer Integrated Orthopaedic Surgery: Connection of Planning and Execution in Surgical Intervention", Computer-integrated surgery: technology and clinical applications, (1996), 451-463.
Radermacher, K, et al., "CT Image-Based Planning and Execution of interventions in Orthopedic Surgery Using Individual Templates, Experimental Results and Aspects of Clinical Applications", Computer Assisted Orthopedic Surgery (CAOS), Hogrefe & Huber Publishers, (1995); 42-52.
Radermacher, K, et al., "Image Guided Orthopedic Surgery Using Individual Templates", Springer Berlin/Heidelberg, CVRMed-MRCAS'97, vol. 1205, (1997), 606-615.
Radermacher, K, et al, "Technique for Better Execution of CT Scan Planned Orthopedic Surgery on Bone Structures", British Library—"The world's knowledge" 2nd Congress of ISCAS Conference, (Jun. 1995), 933-938.

(56) References Cited

OTHER PUBLICATIONS

Radermacher, Klaus, et al., "Computer Assisted Orthopaedic Surgery with image Based Individual Templates", Clinical Orthopaedics and Related Research No. 354, Lippincott Williams & Wilkins, (Sep. 1998), 28-38.
Sharp, Michael S, "Patient-Specific, Resurfacing Bi-Compartmental Arthuroplasty Futuretech", Orthopaedic Product News, (Apr. 2008), 12-15.
Sisto, Domenick J, et al., "Custom Patellofemoral Arthroplasty of the Knee Surgical Technique", Journal of Bone and Joint Surgery, vol. 89-A, (2007), 214-225.
Slamin, John, et al., "Do You Have This Implant in My Size?", MDT Medical Design Technology, [Online]. Retrieved from the Internet: <http://www.mdtmag.com/scripts/ShowPR.asp?PUBCODE=046&ACCT=0007796& ISSUE...>, (Jul. 31, 2008), 3 pgs.
Steinwachs, Matthias Reinhard, "Cartilage Repair—Autologous Chondrocyte Transplantation and Autologous Matrix-induced Chondrogenesis", European Musculoskeletal Review, (2006), 65-68.
Thoma, W, et al., "Endoprothetischen Versorgung des Kniegelenks auf der Basis eines 3D-computertomographischen Subtraktionversfahrens", (2000), 641-644.
"U.S. Appl. No. 14/798,809, Advisory Action dated Feb. 28, 2018", 3 pgs.
"U.S. Appl. No. 14/798,809, Final Office Action dated Dec. 29, 2017", 4 pgs.
"U.S. Appl. No. 14/798,809, Preliminary Amendment filed Oct. 29, 2015", 7 pgs.
"U.S. Appl. No. 14/798,809, Response filed Feb. 21, 2018 to Final Office Action dated Dec. 29, 2017", 7 pgs.
"U.S. Appl. No. 14/798,809, Response Filed Mar. 29, 2018 to Advisory Action dated Feb. 28, 2018", 8 pgs.

* cited by examiner

PATIENT-SPECIFIC GUIDE FOR PARTIAL ACETABULAR SOCKET REPLACEMENT

CROSS-REFERENCE TO RELATED APPLICATIONS

This application is a divisional of U.S. patent application Ser. No. 13/088,787, filed Apr. 18, 2011, which is a continuation-in-part application of U.S. patent application Ser. No. 12/893,306, filed Sep. 29, 2010, now issued as U.S. Pat. No. 9,113,971. The entire disclosures of which are incorporated herein by reference in their entirety.

INTRODUCTION

The present teachings provide a patient-specific guide and an associated implant and methods for preparing the acetabulum to receive a partial acetabular socket replacement. The patient-specific guide and implant are prepared preoperatively for the specific patient based on medical scans of the relevant anatomy of the patient.

SUMMARY

This section provides a general summary of the disclosure, and is not a comprehensive disclosure of its full scope or all of its features.

The present teachings provide a device for partial acetabular replacement that includes a patient-specific acetabular guide. The acetabular guide has a first surface configured to nestingly mate in only one position to the patient's acetabulum. The acetabular guide includes a patient-specific guiding formation configured to guide a cutting tool to remove damaged tissue from a defect of the patient's acetabulum and prepare a patient-specific implantation slot corresponding to the defect after removal of the damaged tissue. In some embodiments, a patient-specific partial acetabular implant can be configured to nestingly mate with the patient-specific implantation slot.

The present teachings also provide a method for a partial socket replacement. The method includes mounting a patient-specific acetabular guide on an acetabulum of a patient and guiding a cutting tool through a patient-specific bore of the acetabular guide. The acetabular guide is configured to mate to the patient's acetabulum in only one position and the patient-specific bore of the acetabular guide is configured to overlay a defect in the acetabulum of the patient. The method includes removing damaged tissue of the defect, and forming a patient-specific implantation slot by removing the damaged tissue. A patient-specific partial acetabular implant can be configured to nestingly mate with the patient-specific implantation slot.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 2:
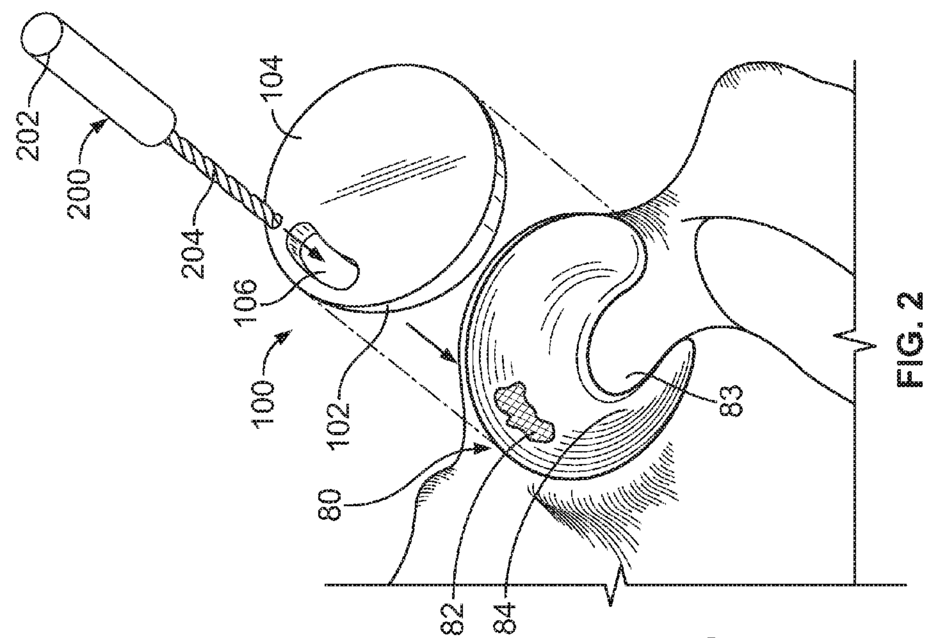
FIG. 2 is another exploded environmental perspective view of the patient-specific guide of FIG. 1.

Exemplary embodiments will now be described more fully with reference to the accompanying drawings.

The present teachings generally provide a patient-specific (custom) guide, and associated implant and method for partial arthroplasty, including partial acetabular socket replacement, partial glenoid socket replacement or other similar procedure. More specifically, the present teachings provide a patient-specific guide for the acetabulum of the patient, when the acetabulum includes a defect that can be corrected by a partial socket replacement or a partial implant.

Generally, patient-specific devices can be designed preoperatively using computer-assisted image methods based on three- or two-dimensional images of the patient's knee anatomy reconstructed from MRI, CT, ultrasound, X-ray, or other three- or two-dimensional medical scans of the patient's anatomy and in some cases complemented with digital photography methods and/or anthropometry databases. Various CAD programs and/or software can be utilized for three-dimensional image reconstruction, such as, for example, software commercially available by Materialise USA, Plymouth, Mich.

Various alignment guides and pre-operative planning procedures are disclosed in commonly assigned and co-pending U.S. patent application Ser. No. 11/756,057, filed on May 31, 2007, U.S. patent application Ser. No. 12/211,407, filed Sep. 16, 2008; U.S. U.S. patent application Ser. No. 11/971,390, filed on Jan. 9, 2008, U.S. U.S. patent application Ser. No. 11/363,548, filed on Feb. 27, 2006; U.S. U.S. patent application Ser. No. 12/025,414, filed Feb. 4, 2008, U.S. patent application Ser. No. 12/571,969, filed Oct. 1, 2009, and U.S. U.S. patent application Ser. No. 12/955,361, filed Nov. 29, 2010. The disclosures of the above applications are incorporated herein by reference.

In the preoperative planning stage for a partial socket replacement, imaging data of the relevant anatomy of a patient can be obtained at a medical facility or doctor's office, using one of medical imaging methods described above. The imaging data can include, for example, various medical scans of a relevant joint portion or other relevant portion of the patient's anatomy, as needed for joint modeling and, optionally, for implant alignment axis determination or for other alignment purposes. The imaging data thus obtained and other associated information can be used to construct a three-dimensional computer image of the joint or other portion of the anatomy of the patient.

According to the present teachings, the patient-specific guides and implants are generally configured to match the anatomy of a specific patient and are generally formed using computer modeling based on the patient's reconstructed three-dimensional anatomic image. The patient-specific guides have an engagement surface that is made to conformingly contact and match a three-dimensional image/model of the patient's bone surface (with or without cartilage or other soft tissue), by the computer methods discussed above. In this respect, a patient-specific guide can nestingly mate with the corresponding bone surface (with or without articular cartilage) of the specific patient in only one position.

According to the present teachings, the patient-specific guide can include a custom-made (patient-specific) guiding formation, such as, for example, a guiding bore for guiding a joint preparation tool, such as a reamer, cutter, broach, mill, drill or other cutting tool, according to the pre-operative plan for the patient. In some embodiments, the guiding formation can have a patient-specific size and shape configured during the preoperative plan for the patient to guide a milling tool, a reamer, a broach or other cutting tool, as discussed below. The preoperative plan can include planning for bone or joint preparation, including extent and area for defect removal, by milling, reaming, broaching or other cutting method, as well as implant selection and fitting.

The patient-specific guide described herein can be manufactured by various stereolithography methods, selective laser sintering, fused deposition modeling or other rapid prototyping methods. The patient-specific guide can be made of any biocompatible material, including metal, metal alloys or plastic. Generally, the patient-specific guide is disposable and made of lightweight materials, including polymers. The patient-specific implant can be made of any biocompatible materials, including metals and alloys. The patient-specific guide, implant and associated tools can be sterilized and shipped to the surgeon or medical facility in a kit for a specific patient and surgeon for use during the surgical procedure.

Figure 1:
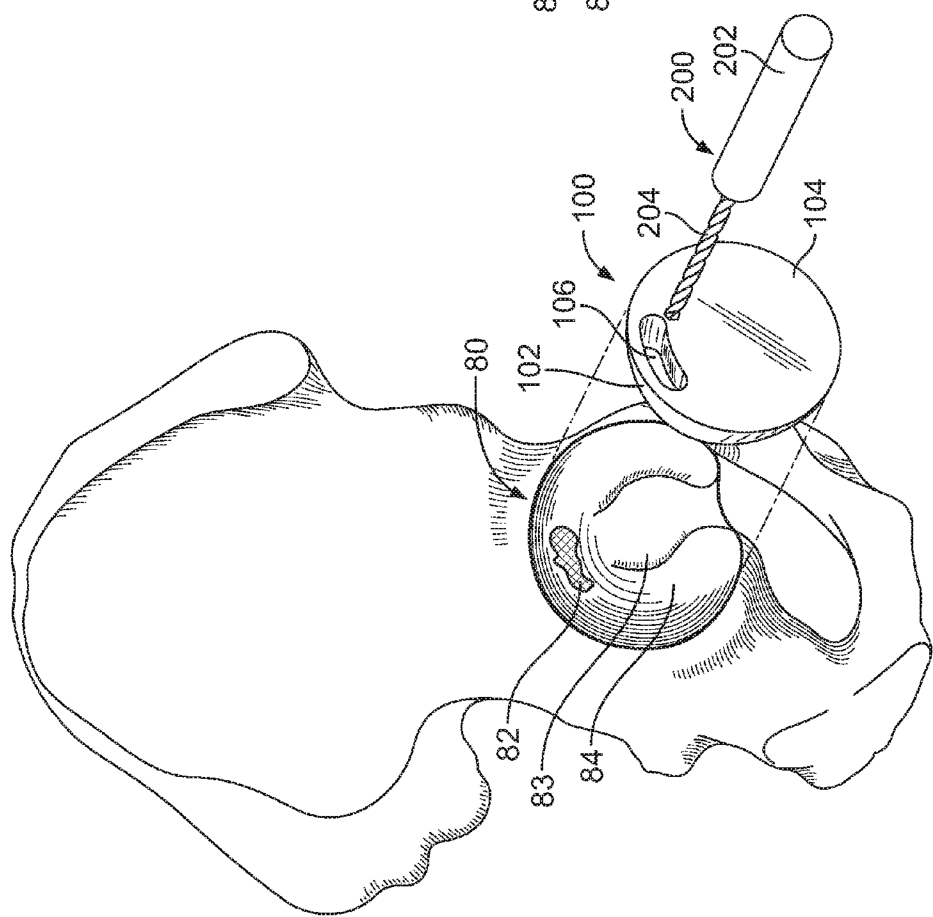
FIG. 1 is an exploded environmental perspective view of a patient-specific guide according to the present teachings.
Figure 4:
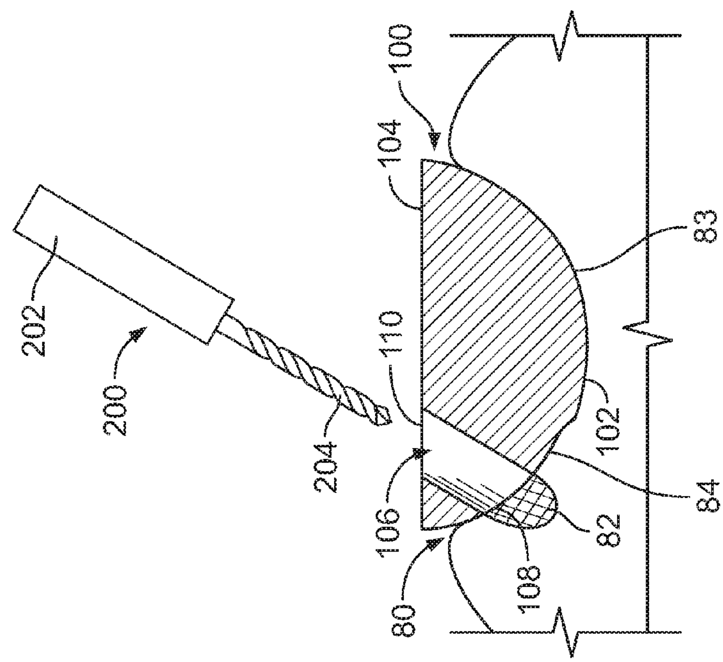
FIG. 4 is an environmental sectional view of the patient-specific guide of FIG. 1.
Figure 5:
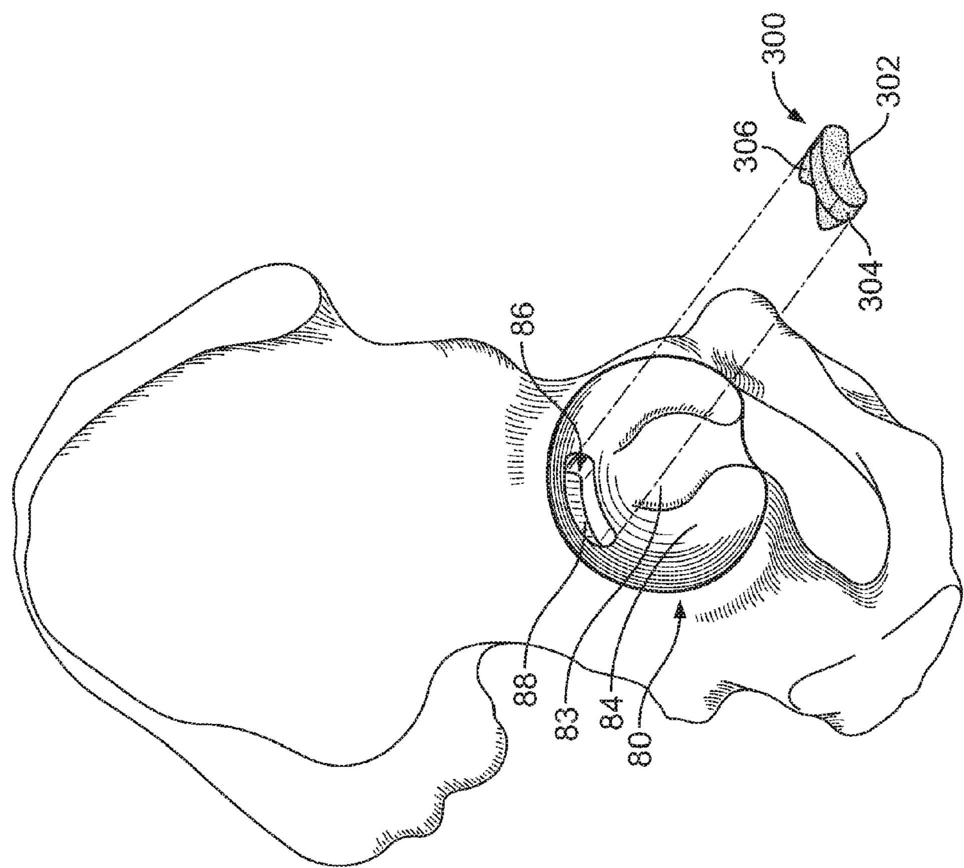
FIG. 5 is an exploded environmental view of an implant according to the present teachings.
Figure 6:
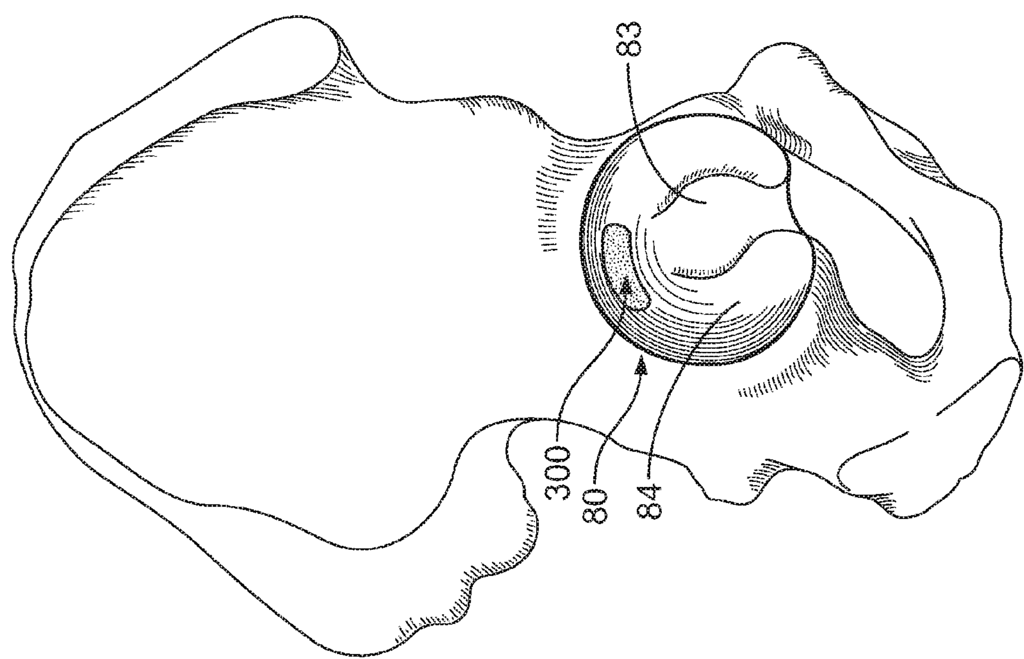
FIG. 6 is an environmental view of the implant of FIG. 5.

Referring to FIGS. 1-6, a patient-specific acetabular guide 100 for preparing an acetabulum to receive a partial acetabular implant 300 (partial acetabular socket replacement) is illustrated. As shown in FIG. 1, the acetabulum of the pelvis of the patient includes an articular cartilage 84 and an acetabular fossa 83 in the acetabulum or acetabular socket 80. A representative defect, such as damaged cartilage, is illustrated at 82. The patient-specific acetabular guide 100 is designed during the preoperative plan of the patient for the specific patient. The patient-specific acetabular guide 100 is configured to guide a cutting tool 200 to mill, burr or otherwise remove the damaged tissue of the defect 82 and prepare the acetabulum 80 for receiving a partial acetabular implant 300. The cutting tool 200 can include a handle 202 and a cutting portion or cutting shaft 204, as shown in FIGS. 1 and 2. The partial acetabular implant 300, shown in FIGS. 5 and 6, is also designed during the preoperative plan in coordination with the patient-specific acetabular guide 100. As described below, the partial acetabular implant is also patient-specific, although non custom implants can be used, if desired, by selecting an appropriate size and shape from a non-custom database during the preoperative planning stage.

Figure 3:
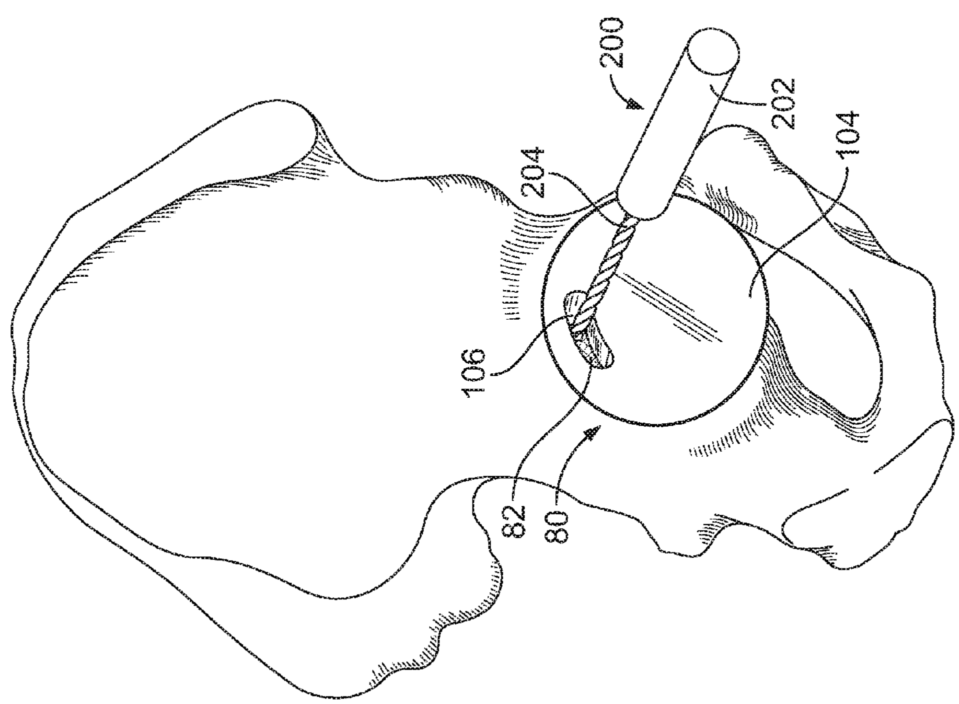
FIG. 3 is an environmental perspective view of the patient-specific guide of FIG. 1.

With continued reference to FIGS. 1-4, the acetabular guide 100 can be formed as a shell having a curved three-dimensional surface 102 (or first surface 102) and bounded by an opposite substantially planar second surface 104. The first surface 102 is patient-specific and designed to nestingly mate with the patient's acetabulum 80, including the articular cartilage 84 and the acetabular fossa 83 only in one position, as shown in FIGS. 3 and 4. In this regard, the patient's acetabulum 80 provides reference landmarks, including, for example, the transition or boundary between the articular cartilage 84 and the acetabular fossa 83 of the specific patient. The acetabular guide 100 includes a patient-specific guiding formation 106 in the form of a through slot or bore that extends between first and second openings 108 and 110 on the first and second surfaces 102, 104 of the acetabular guide 100, as shown in FIG. 4. In some embodiments, the second surface 104 may be omitted such that the acetabular guide 100 is in the form of an open shell and the first opening 108 is the only opening of the guiding formation 106.

The guiding formation 106 is designed during the preoperative plan such that when the acetabular guide 100 can be seated in a unique position in the acetabulum 80 of the patient, the guiding formation 106 can provide a guiding surface for guiding the cutting portion 204 of the cutting tool 200 to remove the damaged cartilage associated with the defect 82. Accordingly, the patient-specific acetabular guide 100 and guiding formation 106 stabilize and guide the cutting tool 200 intraoperatively, enabling the surgeon to remove the damaged tissue associated with the defect 82 and/or other surrounding or underlying tissue in a conservative manner, as determined according to the preoperative plan with the approval of the surgeon. In this regard, the procedure can minimize tissue removal and conserve healthy patient tissue.

Figure 4A:
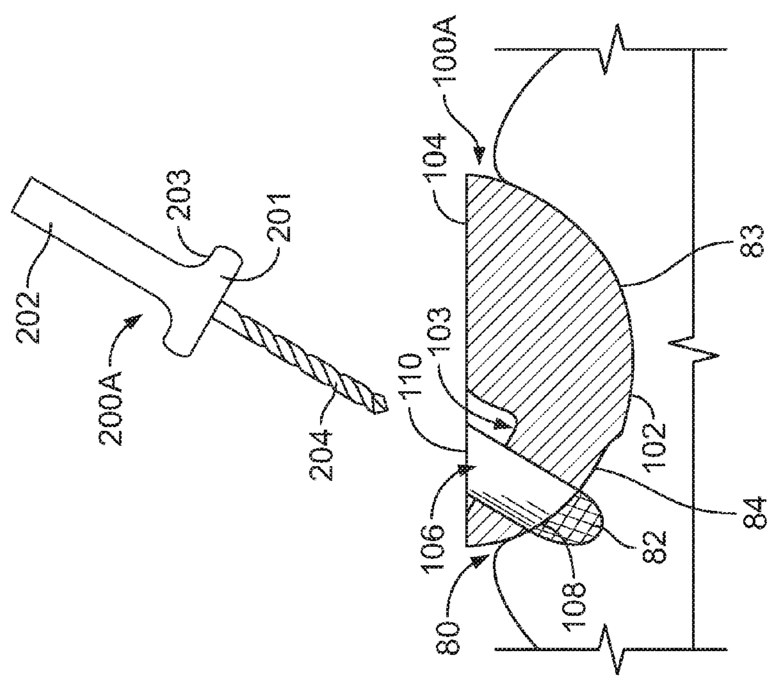
FIG. 4A is an environmental sectional view of a patient-specific guide according to the present teachings.

Referring to FIG. 4A, another embodiment of the acetabular guide 100A with a depth stop or depth control feature is illustrated. The acetabular guide 100A is in other respects similar to the acetabular guide 100, and the description of features common to those of the acetabular guide 100 is not repeated. The depth control feature of the acetabular guide 100A can be, for example, a three dimensional depth control surface 103 extending from the planar second surface 104 of the acetabular guide 100A. The depth control surface 103 is configured to mate with a corresponding outer surface 203 of a distal portion 201 of a handle 202 of a cutting tool 200A, similar in other respects to the cutting tool 200, as shown in FIG. 4A. The position and location of the depth control surface 103 relative to the acetabular guide 100A is determined during the preoperative plan for the patient such that when the outer surface 203 of the handle 202 abuts the depth control surface 103, defect removal and/or cutting by the cutting tool 200A does not exceed a predetermined cutting depth.

Using the cutting tool 200 (or 200A) and acetabular guide 100 (Or 100A), an implant-receiving site 86 is cut, milled or otherwise prepared in the acetabulum 80 of the patient for receiving the partial acetabular implant 300, as shown in FIGS. 5 and 6. The implant-receiving site can be a blind bore formed by removing the defect 82 and having a patient-specific wall 88 that is substantially an envelope of removed defect 82. The acetabular implant 300 can be patient-specific and include a peripheral wall 304 configured to engage the wall 88 of the implant-receiving site or slot 86. The partial acetabular implant 300 includes an outer (articulating) surface 302 configured to continuously transition to the health portion of the articular cartilage 84, replace the damaged cartilage 82 (FIG. 1) and re-create a patient-specific continuous articular cartilage surface without a defect. The partial acetabular implant 300 can include one or more anchoring elements 306, such as pegs, keels, pins or other protrusions, extending from the acetabular implant opposite to the outer surface 302 for anchoring the implant into the acetabulum 80.

It should be appreciated that the wall 88 of the patient-specific implant-receiving site 86 and the peripheral wall 304 of the implant 300 can either follow and match the outline of the original defect 82 or can follow and match a de-burred or smoother envelope of the defect 82. The acetabular implant 300 can be made of any biocompatible material including, for example, pyrocarbon or cobalt chromium alloy with a polished outer surface 304 for articulation with the femoral head of the joint. Additionally, the acetabular implant can be made of allograft tissue, as discussed below in reference to FIGS. 7 and 7A.

Intraoperatively, the patient-specific acetabular guide 100 is mounted on the patient's acetabulum 80 in a unique position determined by the patient's acetabular geometry, which is referenced by the first surface 102 of the acetabular guide, as shown in FIGS. 3 and 4. By design, during the preoperative plan of the patient, the patient-specific guiding formation 106 is configured to be aligned with and overlay the defect 82 when the acetabular guide 100 is seated on the acetabulum. A cutting tool 200 can be guided by the guiding formation 106 to remove the damaged tissue of the defect 82 and create the implantation site 86 for implanting the partial acetabular implant 300. The acetabular implant 300 is then inserted into the implantation site 86 and replaces the damaged tissue of the defect 82.

Example embodiments are provided so that this disclosure is thorough, and fully conveys the scope to those who are skilled in the art. Numerous specific details are set forth such as examples of specific components, devices, and methods, to provide a thorough understanding of embodiments of the present disclosure.

Figure 7A:
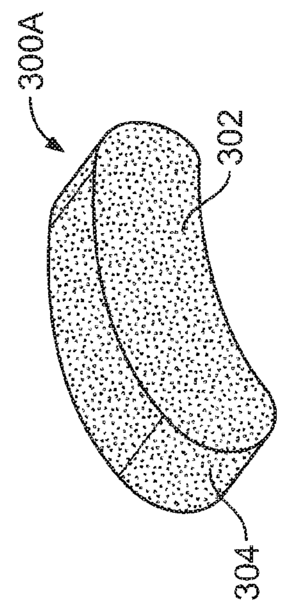
FIG. 7A is a patient-specific implant made from allograft tissue using the inverse patient-specific guide of FIG. 7.
Figure 7:
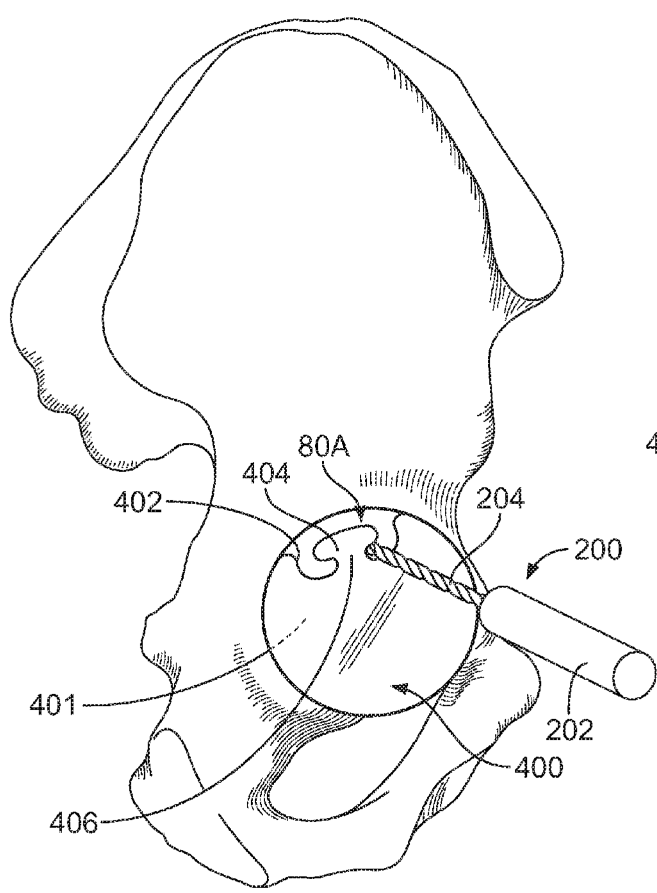
FIG. 7 is an environmental view of an inverse patient-specific guide showing how to make a patient-specific allograft implant from allograft tissue according to the present teachings.
Figure 7B:
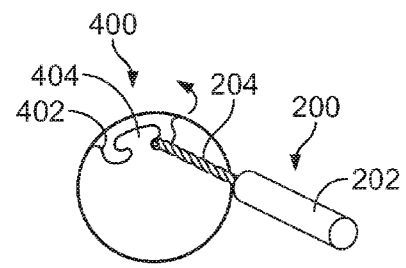
FIGS. 7B-7D are snapshot diagrams of extracting the allograft implant of FIG. 7A using the inverse patient-specific guide of FIG. 7.
Figure 7C:
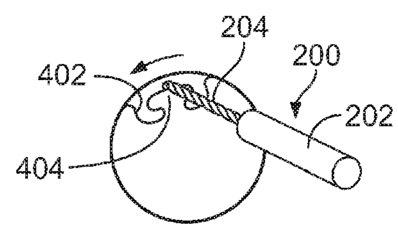
Figure 7D:
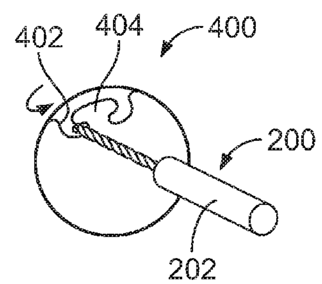

In some embodiments, the partial acetabular implant can be made of allograft tissue. An exemplary partial patient-specific allograft implant 300A (or allograft implant 300A, for short) is illustrated in FIG. 7A. Similarly to the partial acetabular implant 300 of FIG. 5, the allograft implant 300A has a peripheral wall 304 configured to engage the wall 88 of the implant-receiving site or slot 86. The allograft implant 300A includes an outer (articulating) surface 302 configured to continuously transition to the health portion of the articular cartilage 84, replace the damaged cartilage 82 (FIG. 1) and re-create a patient-specific continuous articular cartilage surface without a defect.

To extract a patient-specific allograft from allograft tissue, an "inverse" acetabular guide 400 can be used as a guide. The inverse acetabular guide 400 is configured during the preoperative plan of the patient for extracting wherein a patient-specific implant, i.e., the allograft implant 300A, from allograft tissue. The inverse acetabular guide 400 can be shell-like in shape with a curved surface 401 that engages an allograft tissue (such as a cadaveric acetabulum) 80A. An external protrusion 404 is defined by a curved guiding slot 402 through the inverse acetabular guide 400 and is connected to the acetabular guide through a neck portion 406. The guiding slot 402 and protrusion 404 are patient-specific and designed and configured during the preoperative plan for the patient to trace the shape and size of the peripheral wall 304 of the allograft implant 300A. The guiding slot 402 can guide the cutting tool 200 along the guiding slot 402 and around the protrusion 404, as shown in FIGS. 7 and 7A-7C, to cut the allograft portion for the allograft implant 300A having a peripheral wall 304, but still attached to the allograft issue 80A along an uncut portion corresponding to the neck portion 406 of the protrusion 404. The inverse acetabular guide 400 can then be removed and the allograft implant 300A can be separated from the allograft tissue by cutting through any remaining uncut portion.

It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail. Accordingly, individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A device for partial acetabular replacement comprising:

a patient-specific acetabular guide having a first curved three-dimensional surface configured to nestingly mate in only one position to the patient's acetabulum including the acetabulum's articular cartilage and acetabular fossa, the acetabular guide having a patient-specific guiding formation configured to guide a cutting tool to remove a cartilage defect of the patient's acetabulum and prepare the acetabulum for a patient-specific partial acetabular implant;

wherein the acetabular guide includes a second planar outer surface and the guiding formation is an open bore extending from the second surface and through the first surface.

2. The device of claim 1, wherein the guiding formation is a bore through the acetabular guide.

3. The device of claim 1 in combination with a patient-specific partial acetabular implant configured to be received in a patient-specific implantation slot formed by removing the cartilage defect using the acetabular guide.

4. The combination of claim 3, wherein the partial acetabular implant has a three-dimensional peripheral surface configured to mate with a wall of the patient-specific implantation slot.

5. The combination of claim 4, wherein the partial acetabular implant has an outer surface configured to be continuous with a surrounding cartilage after implantation for femoral joint articulation.

6. The combination of claim 4, wherein the partial acetabular implant includes an anchoring element for engaging the acetabulum of the patient.

7. The combination of claim 3, wherein the partial implant is an allograft implant.

8. The combination of claim 3, further including an inverse acetabular guide configured during the preoperative plan of the patient for extracting the partial acetabular implant from allograft tissue.

9. The device of claim 1, wherein the patient-specific acetabular guide includes a depth control surface configured to mate with a distal portion of a handle of a cutting tool for controlling a cutting depth through the guiding formation.

10. A device for partial acetabular replacement comprising:

a patient-specific acetabular guide having a first surface configured to nestingly mate in only one position to the patient's acetabulum and a patient-specific guiding formation configured to guide a cutting tool to remove damaged tissue from a defect of the patient's acetabulum and prepare a patient-specific implantation slot corresponding to the defect after removal of the damaged tissue; and a patient-specific partial acetabular implant configured to nestingly mate with the patient-specific implantation slot.

11. The device of claim 10, wherein the first surface is a curved three-dimensional surface configured to mate with portions of an articular cartilage and an acetabular fossa of the acetabulum.

12. The device of claim 10, wherein the guiding formation is a bore through the acetabular guide.

13. The device of claim 10, wherein the acetabular guide includes a second planar outer surface and the guiding formation is an open bore extending from the second surface and through the first surface.

14. The device of claim 10, wherein the partial acetabular implant has a three-dimensional peripheral surface configured to mate with a wall of the patient-specific implantation slot.

15. The device of claim 14, wherein the partial acetabular implant has an outer surface configured to be continuous with a surrounding cartilage after implantation for femoral joint articulation.

16. The device of claim 14, wherein the wall of the patient-specific implantation slot is configured as an envelope of the defect.

17. The device of claim 13, wherein the partial acetabular implant includes an anchoring element for engaging the acetabulum of the patient.

18. The device of claim 10, further comprising an inverse acetabular guide configured during a preoperative plan of the patient for extracting the patient-specific partial acetabular implant from allograft tissue.

19. A device for partial acetabular replacement comprising:

a patient-specific acetabular guide having a first curved three-dimensional surface configured to nestingly mate in only one position to the patient's acetabulum including the acetabulum's articular cartilage and acetabular fossa, the acetabular guide having a patient-specific guiding formation configured to guide a cutting tool to remove a cartilage defect of the patient's acetabulum and prepare the acetabulum for a patient-specific partial acetabular implant;

wherein the patient-specific acetabular guide includes a depth control surface configured to mate with a distal portion of a handle of a cutting tool for controlling a cutting depth through the guiding formation.

* * * * *